United States Patent [19]

Ganguly et al.

[11] 4,436,729

[45] Mar. 13, 1984

[54] 23-DEMYCINOSYLTYLOSIN COMPOUNDS, PHARMACEUTICAL COMPOSITIONS AND METHOD OF USE

[75] Inventors: Ashit K. Ganguly, Upper Montclair; Yi-Tsung Liu, Parsippany; Alan K. Mallams, West Orange, all of N.J.

[73] Assignee: Schering Corporation, Kenilworth, N.J.

[21] Appl. No.: 393,901

[22] Filed: Jun. 30, 1982

[51] Int. Cl.³ .................. A61K 31/71; C07H 17/08
[52] U.S. Cl. .................................... 424/180; 536/7.1
[58] Field of Search ....................... 424/180; 536/7.1

[56] References Cited

U.S. PATENT DOCUMENTS

| | | | |
|---|---|---|---|
| 4,279,896 | 7/1981 | Ganguly et al. | 536/7.1 |
| 4,299,953 | 11/1981 | Hamill et al. | 536/7.1 |
| 4,321,361 | 3/1982 | Baltz et al. | 536/7.1 |
| 4,321,362 | 3/1982 | Baltz et al. | 536/7.1 |
| 4,334,019 | 6/1982 | Baltz et al. | 435/76 |

*Primary Examiner*—Johnnie R. Brown
*Attorney, Agent, or Firm*—Anita W. Magatti; Gerald S. Rosen

[57] ABSTRACT

There are disclosed novel 23-demycinosyltylosin and derivatives thereof which have improved activity as antibiotics. Methods of preparation of the compounds are also disclosed.

47 Claims, No Drawings

23-DEMYCINOSYLTYLOSIN COMPOUNDS, PHARMACEUTICAL COMPOSITIONS AND METHOD OF USE

This invention relates to a novel class of macrolide antibacterial agents. More particularly, this invention relates to 23-demycinosyltylosin antibacterials and derivatives thereof.

Demycinosyl- and demycinosyloxy-tylosin and acyl derivatives thereof are known in the antibiotic art. For instance, U.K. Published patent application No. 2,077,730 discloses 23-demycinosyloxytylosin and its esters and U.K. Published patent application No. 2,077,731 descloses 23-demycinosyltylosin and its esters.

We have now discovered that certain 23-demycinosyltylosins and derivatives thereof possess potent and broad spectrum antibacterial activity against gram-positive strains and are better absorbed than the compounds previously known in the art.

In its composition of matter aspect, the present invention embraces compounds of the formula I:

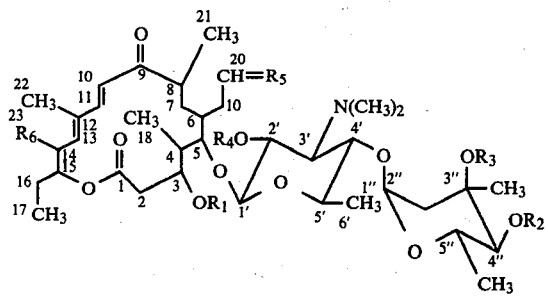

wherein
$R_1$ is hydrogen or acyl;
$R_2$ is acyl;
$R_3$ is hydrogen or acyl; or $R_2$ and $R_3$ are together a carbonyl group linking the 3"- and 4"-hydroxyl groups;
$R_4$ is hydrogen or acyl;
$R_5$ is selected from the group consisting of

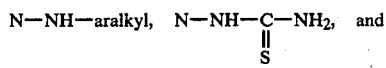

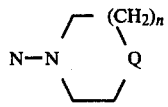

wherein
n is 0-2, and Q is selected from the group consisting of $CH_2$, $CHR_7$, $CHR_8$, $CR_7R_8$, $NR_6$, O, S, $SO_2$, CHOH, $CHOR_7$, $CHOR_8$,

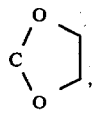

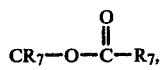

wherein $R_7$ and $R_8$ are independently selected from the group consisting of $(C_1-C_6)$ alkyl, $(C_7-C_{10})$ aralkyl and $(C_6-C_{10})$ aryl including X-substituted aryl and aralkyl, wherein X is halogen, trifluoromethyl, $(C_1-C_6)$ alkoxy, or $(C_1-C_6)$ alkylcarbonyl;

$R_6$ is methyl, hydroxymethyl, fluoromethyl, chloromethyl, bromomethyl, iodomethyl, di$(C_1-C_6)$ alkylamino, acyloxymethyl, CHO or a group of the formula CH=$R_5$ is as hereinbefore defined; and the non-toxic pharmaceutically acceptable acid addition salts thereof.

Although no stereochemical configuration is indicated for the structure above, it is to be understood that the stereochemical configuration is identical to that of tylosin.

The $(C_1-C_6)$ alkyl groups referred to contain 1 to 6 carbon atoms and are exemplified by methyl, ethyl, propyl, butyl, pentyl, hexyl and the corresponding branched-chain isomers thereof.

The $(C_1-C_6)$ alkoxy groups referred to above likewise contain 1 to 6 carbon atoms and are exemplified by methoxy, ethoxy, propoxy and the like.

The term "$(C_6-C_{10})$ aryl" as used herein refers to phenyl and phenyl substituted by one or more substituent groups selected from among halogen, where halogen includes fluoro, chloro and bromo, trifluoromethyl, alkoxy and alkylcarbonyl. Such aryl groups are, for example, 2-fluorophenyl, 2,6-dimethoxyphenyl, 3,4-dichlorophenyl and 3-bromophenyl.

The term "$(C_7-C_{10})$ aralkyl" encompasses aryl substituted lower alkyl groups, such as benzyl, phenethyl, p-fluorobenzyl, o-tolylethyl and m-chlorophenethyl.

The $(C_1-C_6)$ alkylcarbonyl groups contain one to five carbon atoms in the alkyl portion and are exemplified by groups such as acetyl, propionyl, butyryl and the like.

As used herein, the term "acyl" refers to acyl groups derived from such organic acids such as acetic, chloroacetic, propionic, butyric, iso-valeric, alkoxycarbonic, oxalic, oleic, palmitic, stearic, lauric, valeric, benzoic, adamantanecarboxylic, cyclopropanecarboxylic, cyclohexanecarboxylic, β-cyclohexylpropionic, phenylacetic, phenoxyacetic, mandelic, and 2-thienylacetic acids and alkyl-, aryl- and aralkylsulfonic acids, the aryl and aralkyl acids optionally substituted by halogen, nitro, alkoxy and the like on the aromatic moiety. Suitable esters also include hemi-esters derived from dicarboxylic acids such as succinic, maleic, fumaric, malonic, and phthalic acids. Particularly preferred acyl groups are those derived from alkanoic acids of 2 to 5 carbon atoms, such as ecetyl, propionyl, n-butyryl and iso-valeryl.

Particularly preferred compounds of the present invention are those wherein $R_5$ is a group of the formula

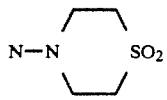

The compounds of the present invention are capable of forming non-toxic, pharmaceutically acceptable acid addition salts with inorganic and organic acids by virtue of the dimethylamino group at position 3'. By "non-toxic pharmaceutically acceptable acid addition salts" is meant those that do not exhibit toxic manifestations at normal therapeutic doses. Exemplary of such salts are those formed with such acids as hydrochloric, sulfuric, phosphoric, citric, acetic, propionic, tartaric, maleic, benzoic, cyclopropylcarboxylic, adamantylcarboxylic, lauryl sulfonic, glucoheptonic, stearic and the like. Acid addition salts may be prepared by methods generally used the art such as by adding a stoichiometric amount of acid to a solution of the antibiotic in a non-reactive organic solvent and isolating the salt by art known methods such as precipitation of the salt with a solvent wherein the salt is not appreciably soluble, e.g. diethyl ether. A non-reactive organic solvent is one which does not react with the antibacterial, the acid or the salt.

In its process aspect, this invention embraces a method of eliciting an antibacterial response in a mammal having a bacterial infection which comprises administering to the mammal a therapeutically effective quantity of a compound as defined in formula I.

In order to elicit an antibacterial effect, the compounds of this invention may be administered orally, topically, intramuscularly or intraveneously. Administration may be effected by any of the conventional methods, i.e., by the use of tablets, capsules, and suspensions, solutions, creams, ointments or injectables. Each of the dosage forms can be formulated utilizing non-toxic pharmaceutically acceptable exicipients conventionally known in the art. The compounds of this invention are preferably administered at from about 5 mg to about 500 mg per kg per day in single or divided doses.

The compounds of this invention are antibacterial agents exhibiting a broad spectrum of activity against gram-positive strains and having significant activity against numerous strains of Staphylococcus, Streptococcus, Bacillus and Sarcina.

The antibacterial activity of compounds of this invention is determined by testing against a variety of pathogens using standard antibiotic dilution assays in Mueller-Hinton Agar, the activity being expressed as the Minimum Inhibitory Concentration (MIC, mcg./ml., 24 hours). The geometric means MICs for many of the compounds of this invention are in the rane of 0.125 to 2.0.

The serum levels of the compounds of the present invention can be determined by administering the compounds either intraveneously, subcutaneously, or orally to the test animals. In general, serum levels are expressed as areas under the curve within a specified time period. The test compounds are generally administered intraveneously at doses of 12.5 mg./kg., or subcutaneously at doses of either 100 mg./kg., or 400 mg./kg. The acute intraveneous toxicities of the compounds of this invention are determined in mice and are expressed as the dose which causes death of 50% of the animals.

The compounds of the present invention can be produced by a variety of multi-step synthesis, originating with tylosin or any of the acylated tylosin derivatives, or the demycinosyltylosins known from the aforementioned British Published applications. Process A is illustrated schematically in Scheme A:

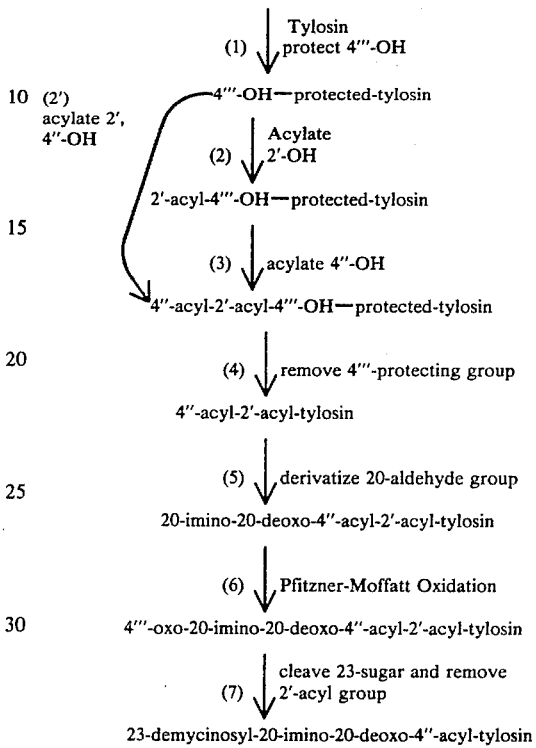

Process A begins by reacting tylosin with a suitable reagent to effect protection of the 4'''-hydroxyl group (Step A1). Although a variety of conventional hydroxyl-protecting groups can be utilized for this purpose (see for instance, U.S. Pat. No. 4,205,163), a highly preferred 4'''-hydroxyl protecting group for use in the present invention has been found to be the tert-butyldimethylsilyl group. As with other such protecting groups, it is most conveniently added to the 4'''-hydroxyl group by reacting the tylosin with tert-butyldimethylsilyl chloride in the presence of an acid acceptor such as imidazole, 4-dimethylaminopyridine, triethylamine or pyridine. Preferably, an anhydrous solvent such as dimethylformamide, dichloromethane or tetrahydrofuran is utilized as the reaction medium. The reaction occurs at temperatures of from about 10°–50° C., with room temperature being satisfactory in most cases. Typical reaction times vary from about 12 to about 48 hours.

Step A2 of Process A involves the introduction of an acyl group at the 2'-hydroxyl position. It is necessary to block this hydroxy group prior to the introduction of any acyl group at the 3'' or 4'' position. Of course, where the acyl group to be introduced at the 4'' position is identical to that of the 2'-acyl group, both may be simultaneously introduced, essentially combining Step A2 and Step A3 of Process A (as indicated in the Scheme A as step A2') simply by increasing the molar quantities of the acylating agent and adding a base such as pyridine as a catalyst. Selective acylation of the 2'-hydroxyl group may be carried out by the conventional methods known for such acylation of common macrolide antibiotics. Acyl groups which may be employed for this purpose, are, for example, a lower alkanoyl group such as an acetyl, propionyl or butyryl group, a lower haloalkanoyl group such as a monochloroacetyl, trichloroacetyl, monobromoacetyl or trifluoroacetyl group, a lower alkoxycarbonyl group such as a methoxycarbonyl or ethoxycarbonyl group, and an aryloxyalkanoyl group such as a phenoxyacetyl group. As the acylating agent, carboxylic acids, acid halides and acid anhydrides corresponding to the acyl groups mentioned above are suitable for use in the process. Acetic anhydride is preferably utilized due to its yield and specificity of reaction. Most preferably, an anhydrous solvent, such as dry acetone is utilized as the reaction medium. Typical reaction temperatures vary from about 10°–50° C., with room temperature being preferred. Typical reaction times vary from about 10–48 hours, depending upon the nature of the specific reactants employed.

Step A3 of Process A concerns the introduction of the 4″-acyl group. The 4″-hydroxy group of the tylosin derivative acylated and protected at the 2′ and 4‴ positions is generally acylated easier than the 3-hydroxy group. When the 4″-hydroxy group is acylated according to the process of the present invention, a slight amount of 3,4″-diacyl derivative is sometimes formed as a by-product depending upon the acylating agent employed. The corresponding acid halides, acid anhydrides or mixed anhydrides with appropriate pivaloic acid are suitably used as the reactive derivatives of carboxylic acid compound in the process of this step. When an acid halide of a carboxylic acid or a mixed acid anhydride is employed as the acylating agent, the reaction of Step A3 is accomplished in the presence of a basic reagent. Preferred basic reagents are pyridine, 4-dimethylaminopyridine, picoline, piperidine and triethylamine, or mixtures thereof. A mixture of triethylamine and 4-dimethylaminopyridine is most highly preferred. Generally, the reaction is carried out in an inert organic solvent such as benzene, toluene, chloroform, dichloromethane, tetrahydrofuran or a mixture thereof. The basic reagent itself can be utilized as a solvent for the reaction. The temperature range is typically between −20° and 50° C., but a higher reaction temperature encourages by-product formation. Generally the preferred reaction temperature is between −10° C. and room temperature. Optionally, the 3″-hydroxyl group can also be acylated at this step. This 3″-hydroxyl group is a tertiary alcohol which reacts only under certain conditions. The 3-hydroxyl group must be blocked, preferably by use of the trimethylsilyl ether derivative, prior to the addition of the 3″-acyl group. Generally, conditions must be more severe, i.e., at higher temperatures, i.e. 60°–100° C., and reaction times somewhat longer. Typically, an acyl chloride is utilized as the acylating agent and tribenzylamine as the basic agent. Any nonpolar, organic solvent is suitable for the conduct of the reaction. Of course, when the 3-position is blocked in a synthetic sequence, it must be deblocked at a later stage after the addition of the 3″-acyl group. Typically this is done after the completion of Step A3, or at any other convenient later stage in the synthetic sequence.

In Step A4 of Process A, the 4‴-hydroxyl protecting group is removed. The exact conditions for removal of course depend upon the nature of the protecting group introduced in Step A1. Such methods are well-known in the art. Where the highly preferred tert-butyldimethyl-silyl group is utilized as the 4‴-hydroxyl protecting group, its removal is conveniently effected by utilizing tetra-n-butylammonium fluoride, or a similar source of fluoride ion. Typically, an anhydrous solvent such as tetrahydrofuran or diethyl ether is utilized as the reaction medium. A non-reactive gaseous atmosphere, such as argon, prevents by-products. Typical reaction temperatures range from 0° to 50° C., with typical reaction temperatures ranging from 1–24 hours.

In Step A5 of Process A, the 20-aldehyde group of the compound is derivatized to the desired 20-imino-20-deoxo-4″-acyl-2′-acyl-tylosin derivative. This is accomplished by reaction of the product of Step A4 with a "1-amino reactant" of the formula $$H_2-R_5$$

wherein $R_5$ is as hereinbefore defined. Many of the "1-amino reactants" herein utilized are commercially available. Those that must be synthesized may be prepared by one of the procedures found in Biel, et.al., *J. Org. Chem.*, 26, 4096 (1961) or Gosl, et. al., *Org. Syn. Collect.*, Vol V, 43 (1963). Generally, the reaction is conducted in a non-polar, anhydrous organic solvent such as benzene, toluene, chloroform, dichloromethane, tetrahydrofuran or a mixture thereof. Reaction temperatures range from about 0°–50° C., with room temperature being preferred. Reaction times vary from 12 hours to 10 days, depending upon the reactants employed.

Step A6 of Process A involves the conversion of the 4‴-hydroxyl group to a 4‴-oxo function. This is accomplished via a Pfitzner-Moffatt Oxidation which utilizes a combination of diethylcarbodiimide or dicyclohexylcarbodiimide with an organic base, such as pyridine and trifluoroacetic acid. Diethylcarbodiimide is preferred due to the water-solubility of its by-product. Typically, 3 equivalents of diethylcarbodiimide, 1 equivalent of organic base and 0.5 equivalent of the trifluoroacetic acid are used. Typical solvents include anhydrous dimethylsulfoxide, benzene, toluene and mixtures thereof. Reaction temperatures vary from 10°–50° C. and typical times range from 2 to 12 hours.

In Step 7 of Process A, both the mycinosyl sugar and the 2′-acyl group are removed to afford the desired 23-demycinosyl-20-imino-20-deoxo-4″-acyl-tylosin. Typically, this is accomplished by dissolving the compound in a mixture of methanol and silica gel and stirring at a temperature of 0°–50° C. (preferably room temperature) for a period of 1–5 days. Process B is illustrated schematically in Scheme B:

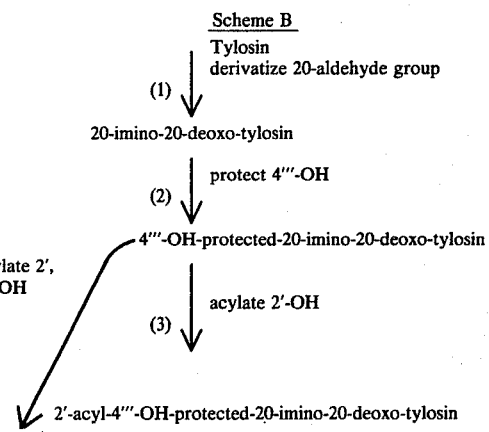

-continued
Scheme B (4) ↓ acylate 4″-OH (and optionally 3″-OH

4″acyl-2′-acyl-4‴-OH-protected-20-imino-20-deoxo-tylosin (5) ↓ remove 4‴-protecting group 4″-acyl-2′-acyl-20-imino-20-deoxo-tylosin (6) ↓ Pfitzner-Moffatt Oxidation 4‴-oxo-2′-acyl-4″-acyl-20-imino-20-deoxo-tylosin (7) ↓ remove mycinose sugar and 2′-acyl group 23-demycinosyl-20-imino-20-deoxo-tylosin Process B employs the same basic reaction steps as Process A, but their order of conduct is rearranged.

Step B1 of the process begins by reacting tylosin with a "1-amino reactant" of the formula $$H_2-R_5$$

wherein $R_5$ is as hereinbefore defined, to effect derivatization of the 20-aldehyde group to a 20-imino-20-deoxo group and thus produce a 20-imino-20-deoxo-tylosin. The reaction conditions employed in this Step B1 are essentially the same as those employed in Step A5 of Process A described above.

The 20-imino-20-deoxo-tylosin is then reacted in Step B2 with a suitable reagent to effect protection of the 4‴-hydroxyl group, thus producing a 4‴-hydroxyl-protected-20-imino-20-deoxo-tylosin. Step B2 employs typical reaction conditions such as those described for Step A1 of Process A. Of course, the 4‴-hydroxyl protecting group may be selected from any of the many well-known in the macrolide art, but, as described above, the tert-butyldimethylsilyl group is highly preferred for use in the present invention.

Having the 20-aldehyde protected as the 20-imino-20-deoxo derivative also has the advantage of eliminating aldehyde-derived by-products formed during the protection of the 4‴-hydroxy group, thus affording significantly higher yields of the desired 4‴-hydroxyl-protected derivatives.

Step B3 of Process B acylates the 2′-hydroxyl group of the compound produced in the previous Step B2 so as to provide a 2′-acyl-4‴-hydroxyl-protected-20-imino-20-deoxo-tylosin. Again, the reaction conditions for this acylation Step are essentially similar to those described above in Step A2 of Process A. Also, as indicated above, where the 2′ and 4″ acyl groups are identical, the acylations of Steps B3 and B4 may be combined in a single Step B3′ simply by increasing the molar quantities of the acylating agent and adding a base such as pyridine as catalyst.

The 2′-acyl-4‴-hydroxyl-protected-20-imino-20-deoxo-tylosin is then acylated at the 4″-hydroxyl position (and optionally the 3″ position) in Step B4 so as to produce a 4″-acyl-2′-acyl-4‴-protected-20-imino-20-deoxo-tylosin. Reaction conditions for the 4″- and 3″-acylations are substantially the same as those described above for Step A3 of Process A. As indicated in Process A, the 3-hydroxyl group should preferably be blocked prior to addition of the 3″-acyl group.

Step B5 of Process B effects removal of the 4‴-hydroxyl protecting group so as to produce the desired 4″-acyl-2′-acyl-20-imino-20-deoxo-tylosin. This reaction is conducted under the same conditions as those utilized in Step A4 of Process A.

Step B6 of Process B, which converts the 4″-acyl-20-imino-20-deoxo-tylosin to a 4‴-oxo-2′-acyl-4″-acyl-20-imino-20-deoxo-tylosin is effected by a Pfitzner-Moffatt Oxidation under essentially the same conditions as described above for Step A6 of Process A.

The final step of Process B, Step B7, effects removal of the 2′-acyl group and the mycinose sugar in a manner essentially the same as that described for Step A7. Process C is illustrated schematically in Scheme C:

Scheme C

Tylosin (1) ↓ derivatize 20-aldehyde group 20-imino-20-deoxo-tylosin (2) ↓ acylate 3,2′,4″ and 4‴-OH groups 3,2′,4″,4‴-tetraacyl-20-imino-20-deoxo-tylosin (3) ↓ add new 4″-acyl group and transacylate old 4″-acyl to 3″-OH 4″-acyl-3,2′,3″,4‴-tetraacyl-20-imino-20-deoxo-tylosin (4) ↓ remove 4‴, 3 and 2′-acyl groups 4″-acyl-3″-acyl-20-imino-20-deoxo-tylosin (5) ↓ Pfitzner-Moffatt Oxidation 4‴-oxo-2′-acyl-4″-acyl-3″-acyl-20-imino-20-deoxo-tylosin (6) ↓ cleave mycinose sugar and 2′-acyl group 23-demycinosyl-4″-acyl-3″-acyl-20-imino-20-deoxo-tylosin Process C begins, as does Process B, by converting tylosin into a 20-imino-20-deoxo-tylosin by reaction with a "1-imino reactant" of the formula $$H_2-R_5$$

wherein $R_5$ is as hereinbefore defined. Reaction conditions for this Step C1 are essentially similar to those described above for Step B1 of Process B.

Step 2 of Process C involves acylation of the 3,2′,4″ and 4‴-hydroxyl groups simultaneously. This is accomplished using reaction times and temperatures similar to those described above for Steps A2 and A3 of Process A and Steps B3 and B4 of Process B, but the molar amounts of acylating agent and basic agent are greatly increased, usually to about 5–20 equivalents. This step thus produces a 3,2',4",4'''-tetraacyl-20-imino-20-deoxo-tylosin.

Step 3 of Process C effects replacement of the 4"-acyl group with a new 4"-acyl group and transacylates the old 4"-acyl group to the 3"-hydroxyl. This transacylation is made possible by the differences in reactivity between the secondary 4"-hydroxyl group and the tertiary 3"-cis hydroxyl group. [See, for instance Jaret et al., *J. Chem. Soc.*, (C), 1374 (1973)]. A large molar excess (typically 5–10 equivalents) of the new acylating agent is utilized as well as temperatures ranging from 80° C. to reflux temperature of the solvent. Typically, pyridine is utilized a the solvent and also performs the role of basic agent so that the reaction is conducted at about 110° C. (reflux of pyridine). Typical reaction times vary from about 12 to 24 hours. This Step C3 thus provides a 4"-acyl-3,2',3",4'''-tetracyl-20-imino-20-deoxo-tylosin where the 4"-acyl group differs from the 3,2',3",4'''-acyl groups.

In Step C4, removal of the 4''', 3 and 2' acyl groups is effected by the addition of an organic base, typically triethylamine. Typical solvents are those such as methanol and typical temperatures in the range of 25°–60° C. The reaction is monitored to determine completion of the removal of the 4''', 3 and 2'-acyl groups and production of the desired 4"-acyl-3"-acyl-20-imino-20-deoxo-tylosin.

Step C5, the Pfitzner-Moffatt Oxidation, is conducted in a manner essentially as described above for Step A6 of Process A.

In Step C6, the mycinose sugar and 2'-acyl groups are removed to afford the desired 23-demycinosyl-4"-acyl-3"-acyl-20-imino-20-deoxo-tylosin. This Step is accomplished according to the method described above for Step A7 of Process A. Process D is illustrated schematically in Scheme D Scheme D
2'-acyl-4'''-OH—protected-20-imino-20-deoxo-tylosin
(prepared as in Scheme B, Step 1 through 3)

-continued
Scheme D (1) ↓ prepare 3",4"-carbonate

2'-acyl-4'''-OH—protected-3",4"-carbonyl-20-imino-20-deoxo-tylosin (2) ↓ remove 4'''-protecting group 2'-acyl-3",4"-carbonyl-20-imino-20-deoxo-tylosin (3) ↓ Pfitzner-Moffatt Oxidation 4'''-oxo-2'-acyl-3",4"-carbonyl-20-imino-20-deoxo-tylosin (4) ↓ remove mycinose sugar and 2'-acyl group 23-demycinosyl-3",4"-carbonyl-20-imino-20-deoxo-tylosin Process D begins, as does Process B, by converting tylosin into a 2'-acyl-4'''-hydroxyl-protected-20-imino-20-deoxo-tylosin utilizing the methods described above for Steps B1 through B3. The 2'-acyl-4'''-hydroxyl-protected-20-imino-20-deoxo tylosin is then converted into a 2'-acyl-4'''-hydroxyl-protected-3",4"carbonyl-20-imino-20-deoxo-tylosin in Step D1. Typically, this conversion is effected by utilizing N,N'-carbonyldiimidazole in an inert solvent such as anhydrous dichloromethane. Typical times vary from 12–30 hours and typical temperatures from about 0°–30° C.

Step D2 of Process D effects removal of the 4'''-hydroxyl group so as to produce the desired 2'-acyl-3",4"-carbonyl-20-imino-20-deoxo-tylosin. This reaction is conducted under the same conditions as those utilized in Step A4 of Process A.

Step D3 of Process D, the Pfitzner-Moffatt oxidation is conducted in a manner essentially the same as described for Step A6 of Process A.

In Step D4, the mycinose sugar and the 2'-acyl groups are removed, as described above for Step A7 of Process A. Process E is illustrated schematically in Scheme E Scheme E
PREPARATION OF 23-DEMYCINOSYLTYLOSIN Tylosin (1) ↓ protect 4'''-OH 4'''-OH—protected-tylosin (2) ↓ form 3,20-hemiacetal and acylate 20,2' and 4"-OH -continued
Scheme E
PREPARATION OF 23-DEMYCINOSYLTYLOSIN

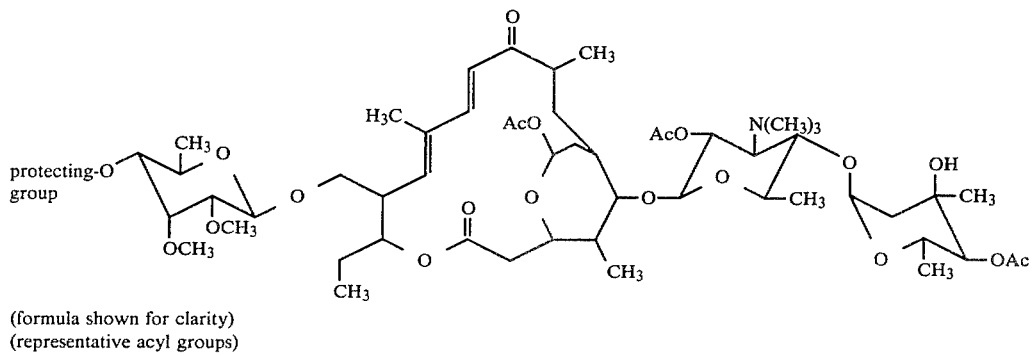

(formula shown for clarity)
(representative acyl groups)

20,2'4''-triacyl-4'''-OH—protected-
tylosin-3,20-hemiacetal (3) | remove 4'''-OH protecting group

↓

20,2'4''triacyl-tylosin-3,20-hemiacetal (4) | Pfitzner-Moffatt Oxidation

↓

4'''oxo-20,2'4''-triacyl tylosin-3,20-hemiacetal

The first step (Step E1) of Process E, begins, as does Process A, by converting tylosin into a 4'''-OH-protected tylosin. The reagents and reaction conditions are identical to those described above in Step A1 of Process A.

Step E2 of Process E converts the 4'''-OH-protected tylosin into a 20,2',4''-triacyl-4'''-OH-protected-tylosin-3,20-hemiacetal by simultaneously forming the 3,20-hemiacetal and acylating the 20, 2' and 4''-hydroxyl groups. This is accomplished by utilizing the appropriate acyl anhydride in excess molar quantity in the presence of a base. Preferred bases are the inorganic bases such as anhydrous potassium carbonate, again utilized in excess molar quantities. Reaction temperatures range from about 50°-100° C., and typical reaction times vary from 5-12 hours.

In Step E3 of Process E, the 4'''-hydroxyl protecting group is removed to afford a 20,2',4''-triacyl-tylosin-3,20-hemiacetal. This is done in a manner essentially identical to that described above for Step A4 of Process A.

Step E4 of Process E is a Pfitzer-Moffatt oxidation which produces a 4'''-oxo-20,2',4''-triacyl-tylosin-3,20-hemiacetal. This step is conducted in a manner substantially identical to those conditions described above for Step A6 of Process A.

In Step E5, the mycinose sugar and the 20,2' and 4''-acyl groups are all simultaneously removed from the 4'''-oxo-20,2',4''-triacyl-tylosin-3,20-hemiacetal so as to afford 23-demycinosyl-tylosin, having the formula

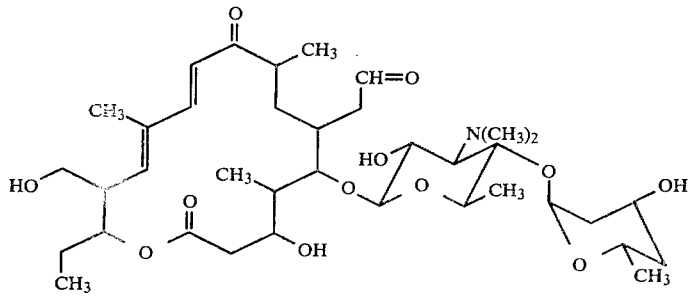

and sometimes hereafter abbreviated 23-DMT. The removal is typically effected by treatment of the 4'''-oxo-20,2',4''-triacyl-tylosin-3,20-hemiacetal with 1-5% methanolic sodium hydroxide for 15-60 minutes at room temperature, followed by dissolution in an alcoholic solvent containing a small amount of an organic base (typically, methanol containing triethylamine) and heating at reflux temperatures for 12-24 hours.

In Step E6 of Process E, the 20-aldehyde group of the 23-demycinosyl-tylosin is derivatized by reaction with a "1-amino reactant" according to the procedure described hereinabove for Step B1 of Process B, thus providing a 20-imino-20-deoxo-23-demycinosyl-tylosin. Process F is illustrated schematically in Scheme F

Scheme F
PREPARATION OF 23-HYDROXY DERIVATIVES

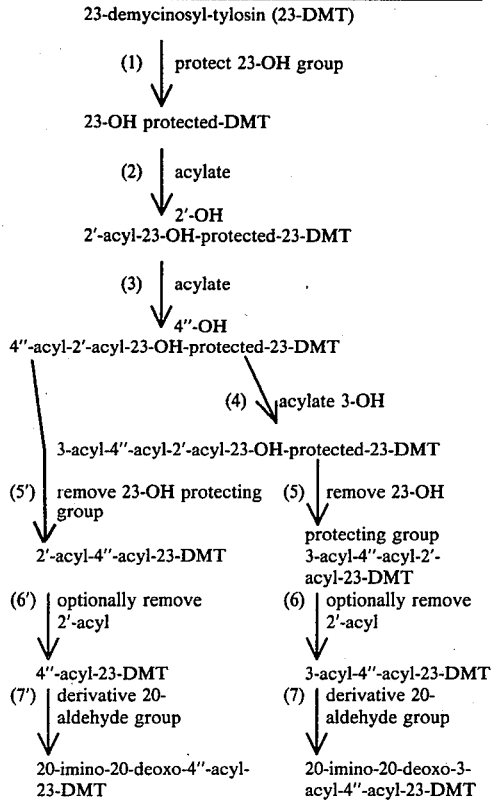

Scheme F begins by protecting the 23-hydroxyl group of 23-demycinosyltylosin. This hydroxyl protection can be accomplished in a number of ways well-known in the art, but, typically, is done by utilizing the preferred protecting group, the tert-butyldimethylsilyl group. As with other such protecting groups, it is most conveniently added to the 23-hydroxyl group by reacting the 23-demycinosyltylosin with tert-butyldimethylsilyl chloride in the presence of an acid acceptor such as imidazole, 4-dimethylaminopyridine, triethylamine or pyridine. Preferably, an anhydrous solvent such as dimethylformamide, dichloromethane or tetrahydrofuran is utilized as the reaction medium. The reaction occurs at temperatures of from about 10°–50° C., with room temperature being satisfactory in most cases. Typical reaction times vary from about 12 to about 48 hours.

Step F2 of Process F involves acylation of the 2'-hydroxyl group. This is accomplished in a manner essentially as described above for Step A2 of Process A.

In Step F3 of Process F, the 2'-acyl-23-OH-protected-23-demycinosyltylosin is acylated at the 4"-hydroxyl position to afford a 4"-acyl-2'-acyl-23-OH-protected-23-demycinosyltylosin. This acylation proceeds in a manner identical to that described above for Step A3 of Process A.

Also, the acylations of Steps F2 and F3 may be combined in a single Step where the 2' and 4"-acyl groups are identical. This is accomplished simply by increasing the molar quantities of the acylating agent and adding a base catalyst such as pyridine.

The acylations of Steps F2, F3 and F4 can be combined in a single step where the 3, 2' and 4"-acyl groups are identical,. This is done by increasing the molar quantities of the acylating agent and adding a base such as pyridine, triethylamine, 4-dimethylaminopyridine, or mixtures thereof.

Step F4 of Process F acylates the 3-hydroxyl group to afford a 3-acyl-4"-acyl-2'-acyl-23-hydroxyl-protected-23-demycinosyltylosin. Typically, 3–7 equivalents of an acylating agent, e.g., acetic anhydride are utilized along with excess equivalents of an organic base such as pyridine or 4-dimethylaminopyridine. A mixture of solvents, such as triethylamine and methylene chloride is often utilized as the reaction medium. Temperatures vary from 10°–50° C., and reaction times from about 18 to 24 hours.

In Step 5 of Process F, the 23-hydroxyl protecting group is removed to afford a 3-acyl-4"-acyl-2'-acyl-23-demycinosyltylosin. Conditions for removal vary, depending upon the nature of the protecting groups utilized. Where the tert-butyldimethylsilyl group is utilized, removal can be suitably effected by treatment with 80% acetic acid in water. Typical temperatures range from 10°–50° C. with room temperature being preferred. Reaction times vary from about 1 to 5 hours, with about 2 hours being generally sufficient for completion of the reaction.

Step F6 of Process F is an optional removal of the 2'-acyl group. Depending upon the nature of the acyl group, removal is typically effected by dissolving the component in methanol and stirring at a temperature of 0° to 50° C., preferably room temperature, for 1 to 5 days to afford a 3-acyl-4"-acyl-23-demycinosyl-tylosin.

In Step F7 of Process F, the 20-aldehyde group of the 3-acyl-4"-acyl-23-demycinosyl-tylosin is derivatized by reaction with a "1-amino reactant" according to the procedures described above for Step B1 of Process B, thus affording the desired 20-imino-20-deoxo-3-acyl-4"-acyl-23-O-demycinosyltylosin, which can optionally contain the 2'-acyl group.

The conduct of Steps F5, F6 and F7 of Process F using 4"-acyl-2'-acyl-23-hydroxyl-protected-23-demycinosyl-tylosin in essentially the same manner as described above for Steps F5, F6 and F7 affords, respectively, a 2'-acyl-4"-acyl-23-demycinosyl-tylsoin, a 4"-acyl-23-demycinosyltylosin, and the 20-imino-20-deoxo-4"-acyl-23-demycinosyltylosin.

Alternatively, Steps F1 through F6 can be carried out using 20-imino-20-deoxo-23-demycinosyltylosin as a starting material to afford the same desired products. Process G is illustrated schematically as follows:

Scheme G
PREPARATION OF 23-HYDROXY DERIVATIVES

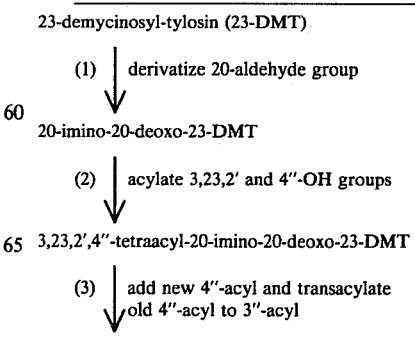

-continued
Scheme G
PREPARATION OF 23-HYDROXY DERIVATIVES

4''-acyl-2,23,2',3''-tetraacyl-20-imino-20-deoxo-23-DMT

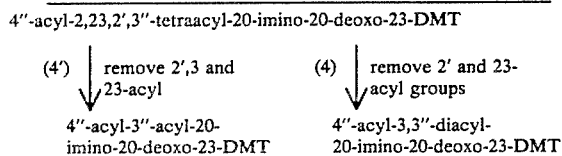

4''-acyl-3''-acyl-20-
imino-20-deoxo-23-DMT                    4''-acyl-3,3''-diacyl-
                                         20-imino-20-deoxo-23-DMT In Step G1 of Process G, the 20-aldehyde group of 23-demycinosyl-tylosin is derivatized by reaction with a "1-amino reactant" according to the procedures detailed above for Step B1 of Process B to afford a 20-imino-20-deoxo-23-demycinosyl-tylosin.

Step G2 of Process G involves the simultaneous acylation of the 3, 23, 2' and 4''-hydroxyl groups to produce a 3, 23, 2', 4''-tetraacyl-20-imino-20-deoxo-23-demycinosyl-tylosin. This may be conveniently done by the addition of a large molar excess (typically 5–15 equivalents) of the acylating agent and a large molar excess (again, 5–15 equivalents) of a base. Suitable bases are the organic bases such as pyridine, triethylamine and 4-dimethylaminopyridine. Solvents include those such as methylene chloride, chloroform and mixtures thereof. Typical reaction times vary from 12–36 hours, while typical temperatures range from about 10°–50° C., with room temperatures being most preferable.

In Step G3 of Process G, a new 4''-acyl group is added, and the old 4''-acyl group transacylated to the 3''-acyl group. This transacylation is accomplished in a manner essentially identical to that described above for Step C3 of Process C and affords a 4''-acyl-3, 23, 2',3''-tetraacyl-20-imino-20-deoxo-23-demycinosyltylosin.

In Step G4 of Process G, the 2' and 23-acyl groups are removed to afford a 4''-acyl-3, 3''-diacyl-20-imino-20-deoxo-23-demycinosyltylosin. This removal is efected by dissolving the compound in methanol and triethylamine and heating gradually from room temperature to about 60°–70° C. Completion of the removal is monitored by thin layer chromatography, at which time the reaction mixture is worked up and the desired product isolated.

As an alternate to Step G4, the reaction may be allowed to continue to effect removal of the 3-acyl group as well as the 2' and 23-acyl groups. This is shown a Step G4' in Scheme G. Conditions are identical to G4 except for length of reaction time and thus is provided a 4''-acyl-3''-acyl-20-imino-20-deoxo-23-O-demycinosyltylosin.

Alternatively, Steps G2, G3, G4 and G4' of Process G may be carried out using 23-demycinosyltylosin as starting material to produce either a 4''-acyl-3''-acyl-23-demycinosyl-tylosin or a 4''-acyl-3''-acyl-23-demycinosyl-tylosin which can then be derivatized at the 20-aldehyde position as described in Step B1 of Process B. This route results in the same compounds as produced by Scheme G. Process H is illustrated schematically as follows:

Scheme H
PREPARATION OF 23-HYDROXY DERIVATIVES
23-demycinosyl-typlosin (23-DMT)

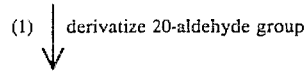

-continued
Scheme H
PREPARATION OF 23-HYDROXY DERIVATIVES
20-imino-20-deoxo-23-DMT

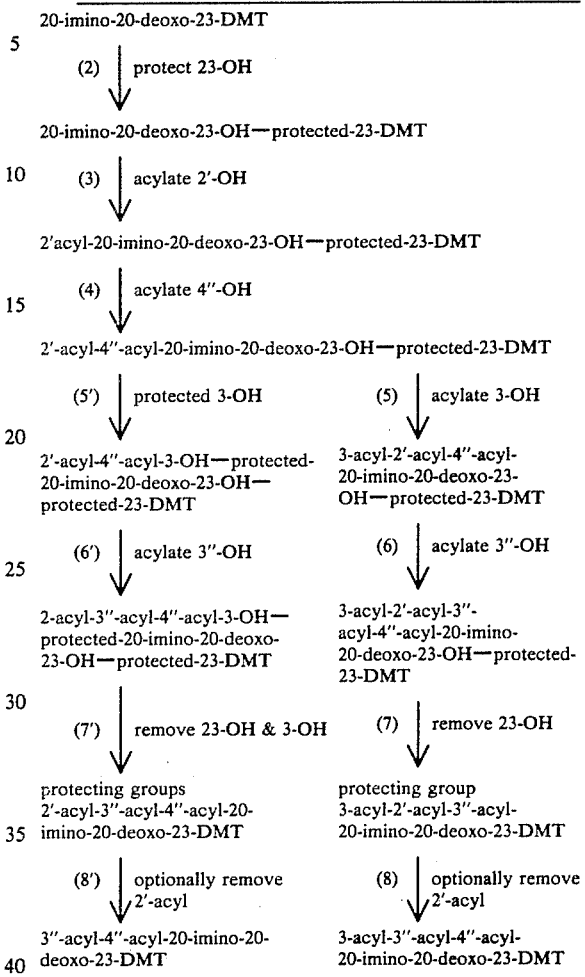

In Step H1 of Process H, the 20-aldehyde group of 23-demycinosyltylosin is derivatized by reaction with a "1-amino reactant" according to the procedures detailed above for Step B1 of Process B to afford a 20-imino-20-deoxo-23-demycinosyltylosin.

Step H2 of Process H involves the protection of the 23-hydroxyl group. Any conventional hydroxyl-protecting group can be utilized for this purposes, but as described above in Step A1 of Process A, a highly preferred group is the tert-butyldimethylsilyl group. Reaction conditions for this protection are essentially as described above in Step A1 of Process A.

Step H3 of Process H involves acylation of the 2'-hydroxyl group of the 20-imino-20-deoxo-23-hydroxyl-protected-23-demycinosyltylosin to afford a 2'-acyl-20-imino-20-deoxo-23-hydroxyl-protected-23-demycinosyltylosin. This is accomplished in a manner essentially as described above for Step A2 of Process A.

In Step H4 of Process H, the 2'-acyl-20-imino-20-deoxo-23-hydroxyl-protected-23-demycinosyltylosin is acylated at the 4''-hydroxyl position to afford a 4''-acyl-2'-acyl-20-imino-20-deoxo-23-hydroxyl-protected-23-demycinosyltylosin. This acylation proceeds in a manner identical to that described above for Step A3 of Process A.

Where the 2' and 4''-acyl groups are identical, the acylations of Steps H3 and H4 may be combined. This is accomplished in a manner substantially the same as described above for Process F.

Step H5 of Process H acylates the 3-hydroxyl group to afford a 3-acyl-2'-acyl-4"-acyl-20-imino-20-deoxo-23-hydroxyl-protected-23-demycinosyltylosin. Reaction conditions for this step are substantially as described above for Step F4 of Process F.

Where the desired 2', 4" and 3-acyl groups in the final product are identical, Steps H3, H4 and H5 may be combined to afford the desired product in a single step. This is accomplished as described above in Process F.

As an alternative, the 3-hydroxyl group can be protected rather than acylated (Step H5'). Again, this is preferably done in the same manner as described above in Step A1 of Process A to afford a 3-hydroxyl-protected-2'-acyl-4"-acyl-20-imino-20-deoxo-23-hydroxyl-protected-23-demycinosyl-tylosin.

Step H6 acylates the 3"-hydroxyl group. Typically, an acyl chloride is utilized as the acylating agent and tribenzylamine as the basic agent. Any nonpolar, organic solvent is suitable for the conduct of the reaction.

In Steps H7 and H7' of Process H, the 23-hydroxyl-protecting group is removed. Due to the presence of the 3-acyl group in Step H7, a milder deprotection medium, such as 80% acetic acid in water, must be utilized. Where the removal of the 3-hydroxyl-protecting group is desired, as in Step H7', the deprotection is accomplished utilizing fluoride ion as described above in Step A4 of Process A.

Step H8 involves the optional removal of the 2'-acyl group. Where such removal is desired, it is accomplished in a manner essentially identical to that described above for Step B6 of Process B to afford either the desired 3-acyl-3"-acyl-4"-acyl-20-imino-20-deoxo-23-demycinosyl-tylosin or a 3"-acyl-4"-acyl-20-imino-20-deoxo-23-demycinosyl-tylson.

Alternatively, Steps H2 through H8 may be carried out utilizing 23-demycinosyl-tylosin as the starting material to afford compounds which can then be derivatized to the 20-imino-20-deoxo compounds. Process I is illustrated schematically in Scheme I.

Scheme I
PREPARATION OF 23-DEOXY DERIVATIVES
23-demycinosyl-tylosin (23-DMOT)
(1) | convert 23-OH to 23-I
↓
20-iodo-23-demycinosyloxy-tylosin (23-iodo-23-DMOT)
(2) | convert 23-ICH₂— to 23-CH₃—
↓

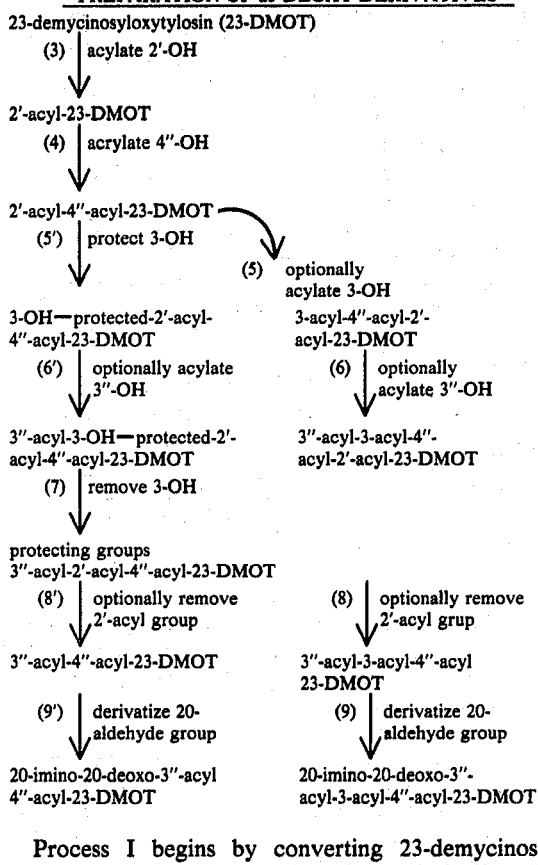

-continued
Scheme I
PREPARATION OF 23-DEOXY DERIVATIVES

Process I begins by converting 23-demycinosyl-tylosin to 23-iodo-23-demycinosyloxy-tylosin (Step I1). Typically, the iodination is accomplished by using an alkoxyphosphonium iodide reagent, for instance, methyl triphenoxyphosphonium iodide. Triphenyl phosphine and iodine may also be utilized. Any anhydrous organic solvent can be utilized, but a polar solvent, such a dimethylformamide, is preferred. Reaction times vary from about 2–10 hours while typical reaction temperatures range from about 10°–50° C., with room temperature being generally preferred.

Optionally the 20-aldehyde group may be protected by any of the conventional means known in the art, for example, as the 20-dimethylacetal, prior to carrying out the iodination reaction. The protecting groups may then be removed to give the 20-aldehyde derivative.

In Step I2 of Process I, the 23-iodo substituent is replaced by a hydrogen atom to afford a 23-methyl group, resulting in the production of 23-demycinosyloxy-ytylosin, having the structure

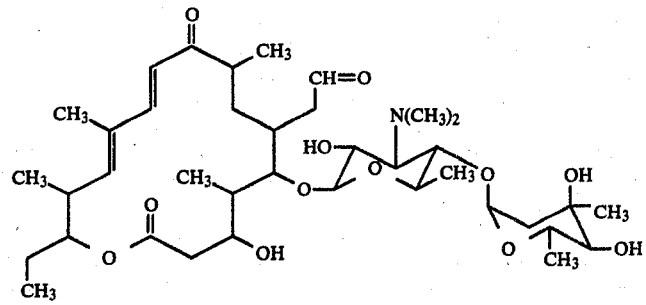

and sometimes hereinafter abbreviated 23-DMOT. This reaction is accomplished by utilizing a suitable deiodination reagent, such as tri-n-butyltin hydride. Preferably, an inert atmosphere is maintained to minimize side reactions. Suitable solvents are any of the anhydrous inert organic solvents, with tetrahydrofuran being preferred. Reaction temperatures range from about 50° C. to reflux temperature of the solvent. Typical times vary from 12 to 24 hours.

Step I3 involves the acylation of the 2'-hydroxyl group to afford 2'-acyl-23-demycinosyloxytylosin. This is conducted in a manner essentially identical to that described above for Step A2 of Process A.

In Step I4, the 4"-hydroxyl-group is acylated according to the procedures detailed above for Step A3 of Process A so as to provide a 4"-acyl-2'-acyl-23-demycinosyloxytylosin.

Following acylation of the 4"-hydroxy group, Step I5 of Process I optionally acylates the 3-hydroxyl group in a manner substantially identical to the process of Step A3 of Process A. (See discussion above in Step A3 of Process A). If the 3-hydroxyl group is acylated, there is produced a 3-acyl-4"-acyl-2'-acyl-23-demycinosyloxytylosin.

Also, the acylations of Steps I4, I5 and I6 may be combined in a single Step where the 3,2' and 4"-acyl groups are identical, simply by increasing the molar quantities of the acylating agent and adding a base such as pyridine, triethylamine, 4-dimethylaminopyridine, or combinations of the above bases, as in Process F.

The acylations of Steps I4 and I5 also may be combined in a single Step where the 2' and 4"-acyl group are identical, simply by increasing the molar quantities of the acylating agent and adding a base such as pyridine as catalyst as described in Process B.

Alternately, as shown in Step I5', the 3-hydroxyl group may be protected with a suitable protecting group, according to the procedures described above for Step A1 of Process A, to produce a 3-hydroxyl-protected-2'-acyl-4"-acyl-23-demycinosyloxytylosin.

In Step I6, the 3"-hydroxyl group is optionally acylated. This proceeds under the conditions described above for the transacylation Step C3 of Process C. Where the acylation of the 3"-hydroxyl group is desired the 3-hydroxyl group must first be acylated or protected.

Step I7 involves the removal of the 3-hydroxyl-protecting group. This is accomplished under the same reaction conditions as described above for Step H7 of Process H.

Steps I8 of Process I involves the optional removal of the 2'-acyl group from the 3-acyl-4"-acyl-3"-acyl-2'-acyl-23-demycinosyloxy-tylosin the 4"-acyl-2'-23-demycinosyloxy-tylosin or the 3"-acyl derivatives of the above. This is done according to the procedures detailed above for Step F6 of Process F.

In Step I9 of Process I, the 20-aldehyde group of the 3-acyl-4"-acyl-23-demycinosyloxy-tylosin and the 4"-acyl-23-demycinosyloxy-tylosin or the 3"-acyl derivatives of the above is derivatized by reaction with a "1-amino reactant". This reaction is conducted in a manner essentially identical to that described above for Step B1 of Process B to afford either the desired 20-imino-20-deoxo-4"-acyl-23-O-demycinosyloxytylosin, the 20-imino-20-deoxo-3-acyl-4"-acyl-23-O-demycinosyloxytylosin or the 3"-acyl derivatives of the above, any of which may contain the optional 2'-acyl group.

Alternatively, a 20-imino-20-deoxo-23-demycinosyloxy (produced by derivatization of the 20-aldehyde group of 23-demycinosyloxytylosin according to the process of Step B1 of Process B) may be acylated as described in Steps F4, F5, F6, F7, F7' to afford the desired 20-imino-20-deoxo-acyl derivatives. Process J is illustrated schematically in

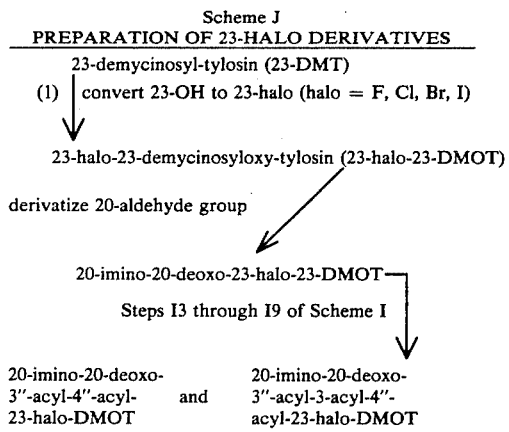

Scheme J
PREPARATION OF 23-HALO DERIVATIVES

In Process J, the first step (Step J1) involves the conversion of the 23-hydroxyl group to a 23-halo substituted where the halo-substituent is fluoro, chloro, bromo or iodo. The 23-iodination is accomplished as previously described for Step H1 of Process H. The 23-chlorination may be conveniently effected by use of any conventional chlorinating agent, with tris-(dimethylamino)-phosphorous amide/carbon tetrachloride being preferred. The use of an anhydrous organic solvent such as dimethylformamide is preferred. Typical times vary from 12–36 hours with typical reaction temperatures ranging from 70°–100° C. The 23-bromination can be accomplished utilizing tris-(dimethylamino)-phosphorous amide/carbon tetrabromide. Again, an anhydrous organic solvent such as dimethylformamide is utilized. Reaction temperatures vary from about −60° to about −30° C., and typical times range from about 0.5 to 2 hours. The 23-fluorination is conducted utilizing 2 equivalents of triphenylphosphine fluoride. Typically, a solvent such as anhydrous acetonitrile is used. Reaction times range from 4–20 hours, while typical temperatures range from 100°–170° C.

The 23-halo-23-demycinosyloxy-tylosin afforded by Step J1 of Process J may then be subjected to the identical reaction steps utilized for 23-demycinosyloxytylosin in Scheme I to produce the desired 20-imino-20-deoxo-3"-acyl-4"-acyl-23-halo-23-demycinosyloxytylosin or 20-imino-20-deoxo-3"-acyl-3-acyl-4"-acyl-23-halo-23-demycinosyloxytylosin, either of which may contain the optional 2'-acyl group.

Optionally, the 20-aldehyde group may be protected and then deprotected after the halogenation as indicated in the discussion of Process I.

Alternately, the 20-aldehyde group of the 23-halo-23-demycinosyloxytylosin can be derivatized first according to the process described above for Step B1 of Process B and then subjected to the acylations described above for Steps F4, F5, F6 and F7 to provide the desired compounds.

Process K is illustrated schematically to Scheme K

Scheme K
PREPARATION OF 23-DIALKYLAMINO DERIVATIVES 23-demycinosyl-tylosin (23-DMT)

(1) ↓ convert 23-OH to 23-I 23-iodo-23-demycinosyloxy-tylosin (23-iodo-23-DMOT)

(2) ↓ derivatize 20-aldehyde group 20-imino-20-deoxo-23-iodo-23-DMOT (3) ↓ convert 23-I to 23-dialkyl amino group 23-dialkylamino-20-imino-20-deoxo-23-DMOT (4) ↓ acylate 2'-OH

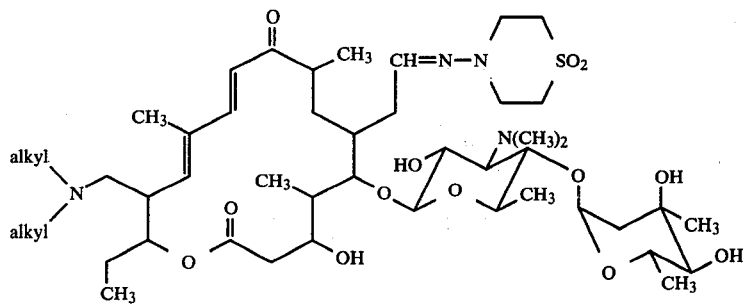

(representative group shown at 20-position)

Step K4 of Process K involves a 2'-hydroxyl-acylation to afford a 2'-acyl-23-dialkylamino-20-imino-20-deoxo-23-DMOT. This is accomplished in a manner substantially identical to that described above for Step A2 of Process A.

In Step K5 of Process K, the 4''-hydroxyl group is acylated to yield a 4''-acyl-2'-acyl-23-dialkylamino-20-imino-20-deoxo-23-O-demycinosyloxytylosin. This reaction is done according to the conditions described above for Step A5 of Process A. Where the desired 2' and 4''-acyl groups are identical, Steps K4 and K5 can be combined as described above for Steps F2 and F3 of Process F.

After acylation of the 4''-hydroxyl group, the 3-hydroxyl group may optionally be acylated in Step K6. (see discussion above in Step A3 of Process A.) If the 3-hydroxyl group is acylated, there is produced a 3-acyl-4''-acyl-2'-acyl-23-dialkylamino-20-imino-20-deoxo-23-demycinosyloxytylosin. This acylation Step K6 may be combined with Steps K4 and K5 where the 2', 4'' and 3-acyl groups are identical as described above for Steps F2, F3 and 4 of Process F.

Alternately, as shown in Step K6', the 3-hydroxyl group may be protected with a suitable protecting group according to the procedures described above for Step A1 of Process A, to produce a 3-hydroxyl-protected-2'-acyl-4''-acyl-23-dialkylamino-20-deoxo-20-imino-23-demycinosyloxytylosin.

In Step K7, the 3''-hydroxyl group is optionally acylated. This proceeds under the conditions described above for the tranacylation Step C3 of Process C. Where the acylation of the 3''-hydroxyl group is desired, the 3-hydroxyl group must first be acylated or protected.

Step K8 involves the removal of the 3-hydroxyl-protecting group. This is accomplished under the same

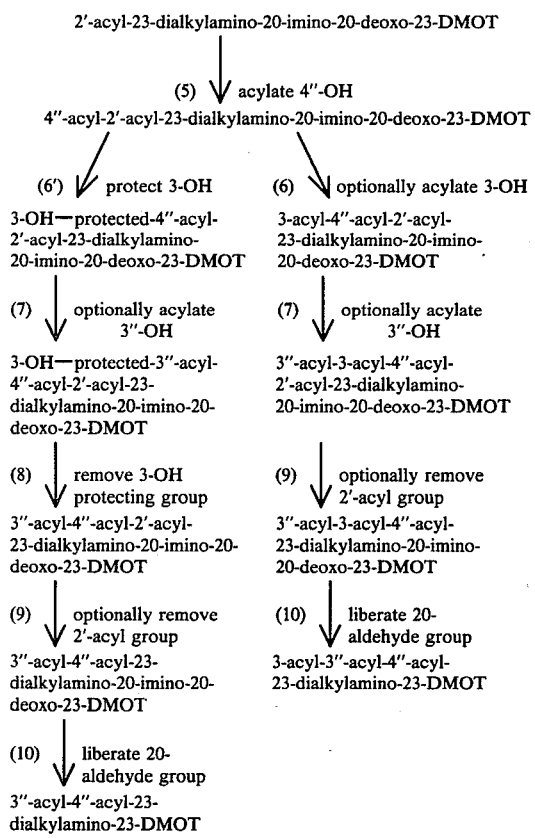

Step K1 of Process K converts 23-O-demycinosyl-tylosin to 23-iodo-23-demycinosyloxytylosin. This conversion is as described above for Step H1 of Process H.

The 20-aldehyde group can, if desired, be protected, then deprotected as discussed with regard to Process I.

In Step K2, the 23-iodo-23-demycinosyloxytylosin is derivatized at the 20-aldehyde position to afford a 20-imino-20-deoxo-23-iodo-23-O-demycinosyloxytylosin. This is done according to the procedure detailed above for Step B1 of Process B.

In Step K3, 20-imino-20-deoxo-23-iodo-23-O-demycinosyoxy-tylosin is reacted with an alkyl amine of the formula

[(C₁–C₆)alkyl]₂NH where the alkyl groups may be alike or different to afford a 23-dialkylamino-20-imino-20-deoxo-23-demycinosyloxytylosin of the formula reaction conditions as described above for Step H7 of Process H.

Step K9 of Process K involves the optional removal of the 2'-acyl group from the 3''-acyl-4'''-acyl-2'-acyl-23-dialkylamino-20-imino-20-deoxo-23-demycinosyloxytylosin, the 3''-acyl-3-acyl-2'-acyl-4'''-acyl-23-dialkylamino-20-imino-20-deoxo-23-demycinosyloxytylosin, the 4'''-acyl-2'-acyl-23-dialkylamino-20-imino-20-deoxo-23-demycinosyloxytylosin, or the 3-acyl-4'''-acyl-2'-acyl-23-dialkylamino-20-imino-20-deoxo-23-demycinosyloxytylosin. This is done according to the procedures detailed above for Step F6 of Process F so as to afford the desired 3''-acyl-4'''-acyl-23-dialkylamino-20-imino-20-deoxo-23-demycinosyloxytylosin, the 4'''-acyl-20-imino-20-deoxo-23-demycinosyloxytylosin, the 3''-acyl-3-acyl-4'''-acyl-23-dialkylamino-20-imino-20-deoxo-23-demycinosyloxytylosin, the 4'''-acyl-23-dialkylamino-20-imino-20-deoxo-23-demycinosyloxytylosin, or the 3-acyl-4'''-acyl-23-dialkylamino-20-imino-20-deoxo-23-demycinosyloxytylosin.

Step K10 of Process K may be carried out by reacting the 23-dialkylamino-20-imino-20-deoxo-23-demycinosyloxytylosin with acetone using silica gel as a catalyst. The reaction may be run at 25° to 60° C. for from 16 to 80 hours to afford the 23-dialkylamino-23-demycinosyloxytylosin derivative.

Process L is illustrated schematically in Scheme L

Scheme L
PREPARATION OF 23-ACYL DERIVATIVES

2'-acyl-4'''-acyl-23-DMT (Prepared as in Step F5' of Process F)

(1) acylate 3 and 23-OH
3,23-di-acyl-2'-acyl-4'''-acyl-23-DMT (2) optionally remove 2'-acyl group
3,23-di-acyl-4'''-acyl-23-DMT (4) optionally acylate 3''-OH
3,23-diacyl-2'-acyl-3''-acyl-4'''-acyl-23-DMT (6) optionally remove 2'-acyl group
3,23-diacyl-3''-acyl-4'''-acyl-23-DMT (7) derivatize 20-aldehyde group
3,23-diacyl-3''-acyl-4'''-acyl-20-imino-20-deoxo-23-DMT (1') acylate 23-OH group
23-acyl-2'-acyl-4'''-acyl 23-DMT (2) optionally remove 2'-acyl group
23-acyl-4'''-acyl-23-DMT (3) protect 3-OH
3-OH—protected-23-acyl-2'-acyl-4'''-acyl-23-DMT (4) optionally acylate 3''-OH
3-OH—protected-23-acyl-2'-acyl-3''-acyl-4'''-acyl-23-DMT (5) remove 3-OH protecting group
23-acyl-2'-acyl-3''-acyl-4'''-acyl-23-DMT (6) optionally remove 2'-acyl group
23-acyl-3''-acyl-4'''-acyl-23-DMT (7) derivatize 20-aldehyde group
23-acyl-3''-acyl-4'''-acyl-20-imino-20-deoxo-23-DMT In Process L, Step L1 begins by acylation of the 3 and 23-hydroxyl groups of a 2'-acyl-4'''-acyl-23-demycinosyltylosin (prepared according to Step F5' of Process F) to afford a 3,23-diacyl-2'-acyl-4'''-acyl-23-demycinosyltylosin. This di-acylation is typically accomplished by utilizing a molar excess of acylating agent, typically 5–15 equivalents, and an excess of an organic base, such as pyridine, 4-dimethylaminopyridine, triethylamine, or mixtures thereof. Typically 5–15 equivalents. An organic solvent such as methylene chloride may be utilized as the reaction medium. Reaction temperatures range from about 10°–50° C., with room temperature being preferred. Reaction times vary from 12–36 hours, depending upon the nature of the particular reactants used.

Alternatively, as shown by Step L1' of Process L, this acylation can be limited to the 23-position by utilizing only a single molar equivalent of the acylating agent, while maintaining the other conditions of the process identical. When only a single equivalent is utilized, there is produced a 23-acyl-2'-acyl-4'''-acyl-23-demycinosyltylosin.

In Step L2 of Process L, the 2'-acyl group is optionally removed to afford either a 3, 23-diacyl-4'''-acyl-23-demycinosyltylosin, or a 23-acyl-4'''-acyl-23-demycinosyltylosin. This removal is accomplished in a manner substantially identical to that described above for Step F6 of Process F.

In Step L3 of Process L, the 3-hydroxyl group can be protected with a suitable protecting group according to the procedures described above for Step A1 of Process A. This step is unnecessary where the 3-hydroxyl group has been acylated as by Step L1.

Step L4 involves the optional acylation of the 3''-hydroxyl group. This proceeds under the conditions described above for the transacylation Step C3 of Process C.

In Step L5 the 3-hydroxyl-protecting group is removed. This is accomplished under substantially the same reaction conditions described above for Step H7 of Process H.

In Step L6 of Process L involves the optional removal of the 2'-acyl group from either the 23-acyl-2'-acyl-3''-acyl-4'''-acyl-23-demycinosyltylosin or the 3,23-diacyl-2'-acyl-3''-acyl-4'''-acyl-23-demycinosyltylosin. This is done according to the procedures detailed above for Step F6 of Process F so as to afford the desired 23-acyl-3''-acyl-4'''-acyl-23-demycinosyltylosin or the 3,23-diacyl-3''-acyl-4'''-acyl-23-demycinosyltylosin.

In Step L7 the 20-aldehyde group is derivatized with a "1-amino reactant" according to the methods disclosed for Step A5 of Process A. This reaction affords either the 23-acyl-3''-acyl-4'''-acyl-20-imino-20-deoxo-23-demycinosyltylosin or the 3,23-diacyl-3''-acyl-4'''-acyl-20-imino-20-deoxo-23-demycinosyltylosin, either of which may also contain the optional 2'-acyl group.

Alternately, the 20-aldehyde group of the 23-acyl-4'''-acyl-23-demycinosyltylosin or the 3,23-diacyl-4'''-acyl-23-demycinosyltylosin can be reacted with a "1-amino reactant" according to the methods disclosed above for Step A5 of Process A. This reaction affords either the desired 3,23-diacyl-4'''-acyl-20-imino-20-deoxo-23-demycinosyltylosin, or the 23-acyl-4'''-acyl-20-imino-20-deoxo-23-demycinosyltylosin, either of which may also contain the optional 2'-acyl group. Those compounds may then be acylated according to the procedures of Steps F4, F5, F6, F7 and F7' to produce the desired compounds of the invention.

Process M is illustrated schematically in Scheme M

Scheme M
PREPARATION OF 23-OXO DERIVATIVES 20-imino-20-deoxo-3-acyl-4''-acyl-2'-acyl-23-DMT
(prepared as in Steps F1 through F7 of Process F, omitting 2'-deacylation)

(1) ↓ Pfitzner-Moffatt Oxidation

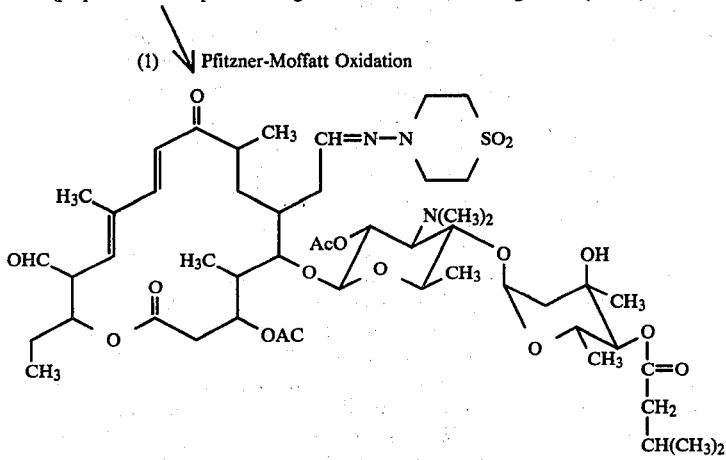

(formula shown for clarity, representative groups)
23-oxo-20-imino-20-deoxo-3-acyl-4''-acyl-2'-acyl-
23-demycinosyloxytylosin ↓ (2) optionally remove 2'-acyl group 23-oxo-20-imino-20-deoxo-3-acyl-4''-acyl-23-
demycinosyloxytylosin (3) ↓ optional derivatization of 23-aldehyde group 20,23-diimino-20,23-dideoxo-23-dehydro-3-acyl-4''-acyl-23-
demycinosyloxytylosin Step M1 of Process M involves a Pfizner-Moffatt Oxidation of a 20-imino-20-deoxo-3-acyl-4''-acyl-2'-acyl-23-O-demycinosyltylosin (prepared as in Steps F1 through F7 of Process F, omitting the 2'-deacylation). This oxidation, conducted essentially as described above for Step A6 of Process A results in the production of a 14-23-oxo-20-imino-20-deoxo-23-dehydro-3-acyl-4''-acyl-2'-acyl-23-demycinosyloxytylosin.

In Step M2 of Process M, the 2'-acyl group is optionally removed according to the procedure described above for Step B6 of Process B.

In Step M3 of Process M, the 14-aldehyde group is derivatized by reaction with a "1-amino reactant" in the same manner as described above for the 20-aldehyde derivatization in Step A1 of Process A. This results in a 20,23-diimino-20,23-dideoxo-23-dehydro-3-acyl-4''-acyl-23-demycinosyloxytylosin, optionally 2'-acylated.

Alternatively the process outlined in Scheme M may be carried out using 20-imino-20-deoxo-2'-acyl-4''-acyl-23-DMT (prepared as in Steps F1 through F7', omitting the 2'-deacylation Step F6), or 20-imino-20-deoxo-2'-acyl-3''-acyl-4''-acyl-23-DMT (prepared as in Steps H1 through H7' of Process H), or 20-imino-20-deoxo-3-acyl-2'-acyl-3''-acyl-4''-acyl-23-DMT (prepared as in Steps H1 through H7 of Process H), as starting materials.

Process N is illustrated schematically in Scheme N

Scheme N
PREPARATION OF 23-OXO DERIVATIVES 3-acyl-2'-acyl-4''-acyl-23-DMT
(prepared as in Steps I1 through I5 of Process I)

(1) ↓ Pfitzner-Moffatt Oxidation 23-oxo-3-acyl-2'-acyl-4''-acyl-23-demycinosyloxytylosin (2) ↓ optionally remove 2'-acyl group 23-oxo-3-acyl-4''-acyl-23-demycinosyloxytylosin (3) ↓ derivatize 20 and 23-aldehyde groups 20,23-diimino-20,23-dideoxo-3-acyl-4''-acyl-23-demycinosyloxytylosin Step N1 of Process N involves a Pfitzner-Moffatt oxidation of a 3-acyl-2'-acyl-4''-acyl-23-demycinosyltylosin (prepared as in Steps I1' through I5 of Process I). This oxidation, conducted esentially as described above for Step A6 of Process A, results in the production of a 23-oxo-2'-acyl-3-acyl-4''-acyl-23-demyinosyloxytylosin.

In Step N2 of Process N, the 2'-acyl group is optionally removed according to the procedure described above for Step B7 of Process B to afford a 23-oxodeoxo-3-acyl-23-demycinosyloxytylosin.

In Step N3 of Process N, the 20 and 23-aldehyde groups are derivatized by reaction with a "1-amino reactant" in the same manner as described above for the 20-aldehyde derivatization in Step A5 of Process A. This results in a 20,23-diimino-20,23-dideoxo-3-acyl-4"-acyl-23-demycinosyloxytylosin.

Alternatively the process outlined in Scheme N may be carried out using a 2'-acyl-4"-acyl-23-DMT (prepared as in Steps F1 through F5' of Process F), or 3-acyl-2'-acyl-3"-acyl-4"-acyl-23-DMT (prepared as in Steps I1 through I8 of Process H where the 20-aldehyde is underivatized), as starting materials.

Throughout all of the above schemes, it is to be understood that the 3"-acyl compounds can be produced by modifying the process to contain the transacylation procedure described above in Step C3 of Process C and Step G3 of Process G.

The following examples describe in detail compounds illustrative of the present invention. It will be apparent to those skilled in the art, that many modifications, both of matrials and methods, may be practiced without departing from the purpose and intent of this disclosure. In these examples, "Rotation" denotes optical rotation; "UV" denotes ultraviolet spectra; "IR" denotes infrared spectra; and "NMR" denotes nuclear magnetic resonance spectra.

EXAMPLE 1

A. 4'''-O-(tert-Butyldimethylsilyl)-tylosin

Tylosin (25 g) and imidazole (18.6 g) are dissolved in dry dimethylformamide (250 ml) and tert-butyldimethylsilyl chloride (19.7 g) is added. The solution is allowed to remain at 25° C. for 19 hours. Then the solution is evaporated to dryness and the residue is taken up in chloroform, washed with water, dried (MgSO$_4$) and filtered. The filtrate is evaporated to dryness and the residue triturated with hot hexane (3×1 l). The insoluble residue is then chromatographed on a silica gel column (160×5 m) using 1.5% methanol in chloroform as the eluant to give 4'''-O-(tert-butyldimethylsilyl)-tylosin, as a colorless, amorphous solid, having characteristics as follows: Rotation: $[\alpha]_D^{26}$-41.8° (CHCl$_3$); UV: $\lambda_{max}$ (CF$_3$CH$_2$OH) 284 nm ($\epsilon$22,616), IR: $\nu_{max}$ (CHCl$_3$) 3500, 2980, 2950, 2910, 1722, 1682, 1600, 1320, 1662, 1220, 1050 cm$^{-1}$; NMR: $\delta$H (CDCl$_3$) 0.14 (3H,s, 4'''-SiCH$_3$), 0.17 (3H,s,4'''-SiCH$_3$), 0.97 (9H,s,4'''-SiC(CH$_3$)$_3$), 1.80 (3H, d, J$_{13,22}$ 1.5 Hz, 22-CH$_3$), 2.50(6H, s, 3'-N (CH$_3$)$_2$) 3.51 (3H,s,2'''-OCH$_3$), 3.62(3H,s,3'''-OCH$_3$), 4.23(1H,d,J$_1$',$_2$' 7.5 Hz, H$_1$'), 4.62(1H,d,J$_1$''',$_2$'''7.5 Hz H$_1$'''), 5.95(1H,dq, J$_{13,22}$ 1.5 Hz, J$_{13,14}$ 10 Hz, H$_{13}$), 6.25(1H, d, J$_{10,11}$ 15 Hz, H$_{10}$), 7.35(1H,d,J$_{10,11}$ 15 Hz, H$_{11}$) and 9.77 (1H,s, H$_{20}$).

B. 2'-O-Acetyl-4'''-O-(tert-butyldimethylsilyl)-tylosin.

4'''-O-(tert-Butyldimethylsilyl)-tylosin (15 g) is dissolved in dry acetone (500 ml) and acetic anhydride (7.4 g) is added. The mixture is allowed to remain at 25° C. for 17 hours. The solution is then evaporated to dryness and the residue azeotroped with toluene to give 2'-O-acetyl-4'''-O-(tert-butyldimethylsilyl)-tylosin as a colorless, amorphous solid. An analytical sample is purified by chromatography on a silica gel column (70×2.5 cm) using 20% acetone in hexane as the eluant. The product has characteristics as follows: Rotation: $[\alpha]_D^{26}$-45.4° (CH$_3$OH); UV:$\lambda_{max}$ (CF$_3$CH$_2$OH) 285 nm ($\epsilon$22,784), IR: $\nu_{max}$ (CDCl$_3$) 3530, 2980, 2960, 2920, 1743, 1720, 1680, 1590, 1230, 1160, 1045 cm$^{-1}$, NMR: $\delta_H$ (CDCl$_3$) 0.10(3H,s,4'''-SiCH$_3$), 0.13 (3H,s,4'''-SiCH$_3$), 0.94(9H,s,4'''-Si C(CH$_3$)$_3$), 1.78(3H,d, J$_{13,22}$ 1.5 Hz, 22-CH$_3$), 2.06(3H,s,2'-OCOCH$_3$), 2.38(6H,s,3'-N(CH$_3$)$_2$), 3.48(3H,s,2'''-OCH$_3$), 3.59(3H,s,3'''-OCH$_3$), 4.27(1H,d,J$_1$',$_2$'7.5 Hz,H$_1$'), 4.60(1H,d,J$_1$''',$_2$''' 8 Hz,H$_1$'''), 5.92 (1H,dq,J$_{13,14}$ 10.5 Hz, J$_{13,22}$ 1.5 Hz,H$_{13}$), 6.25 (1H,d, J$_{10,11}$ 15 Hz, H$_{10}$), 7.31(1H,d,J$_{10,11}$ 15 Hz, H$_{11}$) and 9.65(1H,s,H$_{20}$).

C. 2'-O-Acetyl-4'''-O-(tert-butyldimethylsilyl)-4''-O-iso-valeryltylosin.

2'-O-Acetyl-4'''-O-(tert-butyldimethylsilyl)-tylosin (prepared as in part B of this example) (15.6 g), 4-dimethylaminopyridine (1.85 g) and triethylamine (30 ml) are dissolved in dry dichloromethane (1 l). iso-Valeric anhydride (2.82 g), in dry dichloromethane (200 ml), is added dropwise, with stirring, at 25° C. over one hour. The solution is then stirred for a further 16 hours at 25° C. The solution is washed with water, dried (MgSO$_4$), filtered and evaporated to dryness. The residue is then chromatographed on a silica gel column (160×5 cm) using 30% ethyl acetate in dichloromethane as the eluant to give in order of elution, 2'-O-acetyl-4'''-O-(tert-butyldimethylsilyl)-4''-O-iso-valeryltylosin as a colourless amorphous solid, having characteristics as follows: Rotation: $[\alpha]_D^{26}$ −51.7° (CHCl$_3$), UV: $\lambda_{max}$ (CF$_3$CH$_2$OH) 285 nm ($\epsilon$23,323), IR: $\nu_{max}$(CDCl$_3$) 3520, 2980, 2950, 2900, 1740, 1720, 1675, 1590, 1235, 1160, 1050 cm$^{-1}$; NMR: $\delta_H$ (CDCl$_3$) 0.10(3H,s,4'''-SiCH$_3$), 0.13(3H,s,4'''SiCH$_3$), 0.94(9H,s,4'''-SiC(CH$_3$)$_3$), 0.98(6H,d,J6 Hz, 4''-OCOCH$_2$CH(CH$_3$)$_2$), 1.78(3H,d,J$_{13,22}$ 1.5 Hz, 22-CH$_3$), 2.06(3H,s,2'-OCOCH$_3$), 2.40(6H,s,3'-N(CH$_3$)$_2$), 3.48(3H,s,2'''-OCH$_3$), 3.58(3H,s,3'''-OCH$_3$), 4.25(1H,d,J$_1$',$_2$'7.5 Hz,H$_1$'), 4.59(1H,d,J$_1$''',$_2$'''8 Hz,H$_1$'''), 5.91(1H,dq, J$_{13,22}$ 1.5 Hz,J$_{13,14}$ 10.5 Hz,H$_{13}$), 6.24(1H,d, J$_{10,11}$ 15.5 Hz,H$_{10}$), 7.31(1H,d,J$_{10,11}$ 15.5 Hz,H$_{11}$) and 9.65(1H,s,H$_{20}$), and unreacted 2'-O-acetyl-4'''-O-(tert-butyldimethylsilyl)tylosin.

D. 2'-O-Acetyl-4''-O-iso-valeryltylosin.

2'-O-Acetyl-4'''-O-(tert-butyldimethylsilyl)-4''-O-iso-valeryltylosin (prepared as in part C of this example) (8.25 g) and anhydrous tetra-n-butylammonium fluoride (obtained by azeotroping the trihydrate (2.2 g) with toluene), are dissolved in dry tetrahydrofuran (400 ml) and the solution is allowed to remain at 25° C. for 16 hours under dry argon gas. The solution is evaporated to dryness and the residue taken up in dichloromethane, washed with water, dried (MgSO$_4$), filtered and evaporated to dryness. The residue is chromatographed on a silica gel column (160×2.5 cm) using 40% acetone in hexane as the eluant to give the product, 2'-O-acetyl-4''-O-iso-valeryltylosin as a colourless amorphous solid, having the following chracteristics: Rotation: $[\alpha]_D^{26}$−66.6° (CHCl$_3$); UV: $\lambda_{max}$ (CH$_3$OH) 282 nm ($\epsilon$22,641), IR: $\nu_{max}$ (CDCl$_3$) 3550, 2980, 2950, 2900, 1740, 1735, 1730, 1680, 1600, 1248, 1175, 1065 cm$^{-1}$; NMR:$\delta_H$ (CDCl$_3$), 0.98(6H,d, J 6 Hz, 4''-OCOCH$_2$CH(CH$_3$)$_2$), 1.78(3H,d,J$_{13,22}$ 1.5 Hz,22-CH$_3$), 2.07(3H,s,2'-OCOCH$_3$), 2.41(6H,s, 3'-N(CH$_3$)$_2$), 3.50(3H,s,2'''-OCH$_3$), 3.63(3H,s, 3'''-OCH$_3$), 5.95(1H,dq,J$_{13,22}$ 1.5 Hz,J$_{13,14}$ 10.5 Hz, H$_{13}$), 6.31(1H,d,J$_{10,11}$ 15.5 Hz,H$_{10}$), 7.36(1H,d,J$_{10,11}$ 15.5 Hz,H$_{11}$) and 9.70(1H,s,H$_{20}$).

E. 2'-O-Acetyl-20-deoxo-20-[(4,4-dioxothiomorpholinyl)imino]-4''-O-iso-valeryltylosin.

2'-O-Acetyl-4''O-iso-valeryltylosin (prepared as in part D of this example) (1.8 g) and 1-N-amino-4,4-dioxothiomorpholine (458 mg) are dissolved in dry dichloromethane (50 ml) and the mixture stirred at 25° C. for 212 hours. The solution is evaporated to dryness and the residue chromatographed on a silica gel column (110×2.5 cm) at maximum flow rate using 30% acetone in hexane as the eluant to give 2'-O-acetyl-20-deoxo-20-[(4,4-dioxothiomorpholinyl)-imino]-4''-O-iso-valeryl-tylosin as a colourless amorphous solid, having the following characteristics: Rotation: $[\alpha]_D^{26}$ −71.3° (CHCl$_3$); UV: $\lambda_{max}$ (CH$_3$OH) 240 nm ($\epsilon$8,033), 283 nm ($\epsilon$23,102); IR: $\nu_{max}$ (CDCl$_3$) 3510, 2980, 2950, 2900, 1740, 1720, 1680, 1600, 1223, 1192, 1172, 1130, 1060 cm$^{-1}$; NMR: $\delta_H$ (CDCl$_3$) 0.98(6H,d,J 6 Hz,4''-OCOCH$_2$CH(CH$_3$)$_2$), 1.78(3H,d,J$_{13,22}$ 1.5 Hz, 22-CH$_3$), 2.06(3H,s,2'-OCOCH$_3$), 2.40(6H,s,3'-N(CH$_3$)$_2$), 3.48(3H,s,2'''-OCH$_3$), 3.62(3H,s,3'''-OCH$_3$), 5.90(1H, dq,J$_{13,22}$ 1.5 Hz, J$_{13,14}$ 10 Hz,H$_{13}$), 6.25(1H,d, J$_{10,11}$ 15 Hz,H$_{10}$), 7.97(1H,m,H$_{20}$) and 7.34(1H,d, J$_{10,11}$ 15 Hz,H$_{11}$).

F. 20-Deoxo-20-[(4,4-dioxothiomorpholinyl)-imino]-4'''-oxo-4''-O-iso-valeryltylosin.

2'-O-acetyl-20-deoxo-20-[(4,4-dioxothiomorpholinyl)imino]-4''-O-iso-valeryltylosin (1.4 g.) and dicyclohexyl-carbodiimide (737 mg.) are dissolved in a mixture of dry dimethylsulphoxide (3 ml.) and dry benzene (20 ml.). Pyridine (93 mg.) and trifluoroacetic acid (65 mg.) are added and the mixture is stirred at 25° C. for 5 hours The benzene is evaporated off in vacuo and the residue is taken up in dichloromethane and washed with water. The dichloromethane layer is dried (MgSO$_4$), filtered and evaporated to dryness to give the crude title product.

G. 23-O-Demycinosyl-20-deoxo-20-[(4,4-dioxothiomorpholinyl)imino]-4''-O-iso-valeryltylosin.

The 4'''-ketone (prepared in paragraph F) is dissolved in methanol (250 ml.) and silica gel (14 g.) is added. The mixture is stirred at 25° C. for 168 hours. The silica gel is filtered off and washed with methanol. The combined methanol filtrates are evaporated to dryness and the residue is chromatographed on a silica gel column (160×2.5 cm.) using 35% acetone is hexane as the eluant. The appropriate fractions are combined and re-chromatographed on silica gel plates (20×20 cm.) (250) using 50% acetone in hexane as the eluant. The most polar band affords 23-O-demycinosyl-20-deoxo-20-[(4,4-dioxothiomorpholinyl)-imino]-4''-O-iso-valeryl-tylosin as a colorless, amorphous solid, having the following characteristics: ROTATION: $[\alpha]_D^{26}$ −61.8° (CHCl$_3$); UV:$\lambda_{max}$ (CH$_3$CH$_2$OH) 236 nm ($\epsilon$7,145), 284 nm ($\epsilon$21,172); IR: $\nu_{max}$(CDCl$_3$) 3610, 2980, 2950, 2900, 1725, 1683, 1598, 1325, 1192, 1172, 1130, 1060, 1030 cm.$^{-1}$; NMR: $\delta_H$ (CDCl$_3$) 1.00 (6H,d, J 6 Hz, 4''-OCOCH$_2$CH(CH$_3$)$_2$), 1.84 (3H,d, J$_{13,22}$ 1.5 Hz, 22-CH$_3$), 2.54 (6H, s, 3'-N (CH$_3$)$_2$), 4.31 (1H, d, J$_{1',2'}$ 7.5 Hz, H$_{1'}$), 5.95(1H,dq,J$_{13,22}$ 1.5 Hz, J$_{13,14}$ 10 Hz, H$_{13}$), 6.33(1H,d,J$_{10,11}$ 15.5 Hz, H$_{10}$), 7.06(1H,t,J$_{19, 20}$ 5 Hz, H$_{20}$) and 7.40(1H,d, J$_{10,11}$ 15.5 Hz, H$_{11}$).

EXAMPLE 2

A. 20-Deoxo-20-[(4,4-dioxothiomorpholinyl)imino]-tylosin.

Tylosin (30 g) and 1-N-amino-4,4-dioxothiomorpholine (4.92 g) are dissolved in absolute ethanol (310 ml) and the mixture is stirred at 25° C. for 42 hours. The solution is evaporated to dryness. The residue is then chromatographed on a silica gel column (120×5 cm) using 2% methanol in chloroform as the eluant, followed by rechromatography of the overlap fractions on a silica gel column (120×5 cm) using 1.5% methanol in coloroform as the eluant, to give 20-deoxo-20-[(4,4-dioxothiomorpholinyl)imino]-tylosin as a colorless, amorphous solid, having the following characteristics ROTATION: $[\alpha]_D^{26}$−56.8° (CHCl$_3$); UV: $\lambda_{max}$ (CF$_3$CH$_2$OH) 235 nm ($\epsilon$6,626), 286 nm ($\epsilon$21,765); IR: $\nu_{max}$ (CDCl$_3$) 3580, 2980, 2950, 2900, 1710, 1675, 1585, 1305, 1160, 1120, 1040 cm$^{-1}$; NMR: $\delta_H$ (CDCl$_3$) 0.94(3H,t, J$_{16,17}$ 7 Hz, 17-CH$_3$), 1.02(3H,d,J$_{4,18}$ 6 Hz, 18-CH$_3$), 1.80(3H,d,J$_{13,22}$ 1.5 Hz, 22-CH$_3$), 2.50(6H,s,3'N) (CH$_3$)$_2$), 3.50(3H,s,2'''-OCH$_3$), 3.63(3H,s,3'''-OCH$_3$), 4.29(1H,d,J$_{1',2'}$ 7 Hz,H$_{1'}$), 4.58(1H,d,J$_{1''',2''}$ 7.5 Hz,H$_{1'''}$), 5.94(1H,dq,J$_{13,22}$ 1.5 Hz, J$_{13,14}$ 10 Hz,H$_{13}$), 6.30 (1H,d, J$_{10,11}$ 15.5 Hz, H$_{10}$), 7.01(1H,t,J$_{19,20}$ 5 Hz,H$_{20}$) and 7.37(1H,d,J$_{10,11}$ 15.5 Hz,H$_{11}$).

B. 4'''-O-(tert-Butyldimethylsilyl)-20-deoxo-20-[(4,4-dioxothiomorpholinyl)-imino]-tylosin.

20-Deoxo-20-[(4,4-dioxothiomorpholinyl)-imino]-tylosin (prepared as in part A of this example) (3 g.) and imidazole (975 mg.) are dissolved in dry dimethylformamide (45 ml.) and tert-butyldimethylsilyl chloride (2.16 g.) is added. The mixture is stirred at 25° C. for 18 hours under dry argon gas. The solution is evaporated to dryness and the residue is taken up in dichloromethane, washed with water, dried (MgSO$_4$), filtered and evaporated. The residue is then chromatographed on a silica gel column (30×5 cm.) using 30% acetone in hexane as the eluant to give 4'''-O-(tert-butyldimethylsilyl)-20-deoxo-20-[(4,4-dioxothiomorpholinyl)-imino]-tylosin as a colorless, amorphous solid, having ROTATION: $[\alpha]_D^{26}$−47.1° (CHCl$_3$), UV: $\lambda_{max}$ (CF$_3$CH$_2$OH) 235 nm ($\epsilon$6,710), 286 nm ($\epsilon$23,082); IR: $\nu_{max}$(CDCl$_3$) 3500, 2970, 2940, 2900, 1740, 1680, 1595, 1315, 1260, 1130, 1052 cm.$^{-1}$; NMR: $\delta_H$ (CDCl$_3$) 0.09 (3H,s,4'''-SiCH$_3$), 0.12(3H,s,4'''-SiCH$_3$), 0.94 (9H,s,4'''-SiC(CH$_3$)$_3$), 1.79 (3H,d,J$_{13,22}$ 1.5 Hz, 22-CH$_3$), 2.50(6H,s,3'-N(CH$_3$)$_2$), 3.50 (3H,s,2'''-OCH$_3$),3.61 (3H,s,3'''OCH$_3$), 4.28 (1H,d, J$_{1',2'}$8 Hz, H$_{1'}$), 4.62(1H,d,J$_{1''',2'''}$ 8 Hz, H$_{1'''}$), 5.95 (1H,dq, J$_{13,22}$ 1.5 Hz, J$_{13,14}$ 10 Hz, H$_{13}$), 6.28 (1H,d, J$_{10,11}$ 15.5 Hz, H$_{10}$), 7.00 (1H,t,J$_{19,20}$5 Hz,H$_{20}$) and 7.36 (1H,d,J$_{10,11}$ 15.5 Hz,H$_{11}$).

C. 2',4''-Di-O-Acetyl-4'''-O-(tert-butyldimethylsilyl)20-deoxo-20-[(4,4-dioxothiomorpholinyl)-imino]-tylosin.

4'''-O-(tert-Butyldimethylsilyl)-20-deoxo-20-[(4,4-dioxothiomorpholinyl)-imino]-tylosin (prepared as in Parts A and B of this example) (1.16 g.) is dissolved in dry pyridine (5 ml), and acetic anhydride (1 ml.) is added. The mixture is stirred at 25° C. for 20 hours. The solution is evaporated to dryness and the residue azeotroped with toluene. The residue is taken up in dichloromethane and the latter is washed successively with water and saturated brine, then dried (MgSO$_4$) filtered and evaporated to dryness to give 2', 4''-di-O-acetyl-4'''-O-tert-butyldimethylsilyl)-20-deoxo-20[(4,4-dioxothiomorpholinyl)-imino]-tylosin, a colourless, amorphous solid, having the following characteristics: Rotation: $[\alpha]_D^{26}$−56.3° (CHCl$_3$); UV: $\lambda_{max}$ (CF$_3$CH$_2$ OH) 234 nm ($\epsilon$6,433), 286 nm ($\epsilon$20,760); IR: $\nu_{max}$ (CDCl$_3$) 3510, 2975, 2950, 2900, 1740, 1685, 1595, 1317, 1240, 1175 1130, 1050, cm.$^{-1}$, NMR: $\delta_H$ (CDCl$_3$) 0.12 (3H,s,4'''-SiCH$_3$), 0.15 (3H,s,4'''-SiCH$_3$), 0.93 (9H,s,4'''-SiC(CH$_3$)$_3$), 1.80 (3H,d,J$_{13,22}$ 1.5 Hz, 22-CH$_3$), 2.10 (3H,s,2'-OCOCH$_3$), 2.18 (3H,s,4''-OCOCH$_3$), 2.44 (6H,s,3'-N(CH$_3$)$_2$), 3.52 (3H,s,2'''-OCH$_3$), 3.63 (3H,s,3'''-OCH$_3$), 6.00 (1H,dq, J$_{13,22}$ 1.5 Hz, J$_{13,14}$ 10 Hz,H$_{13}$), 6.32 (1H,d, J$_{10,11}$ 15 Hz,H$_{10}$), 7.00 (1H,t,J$_{19,20}$5 Hz, H$_{20}$) and 7.40 (1H,d,J$_{10,11}$ 15 Hz,H$_{11}$).

D. 2',4''-Di-O-acetyl-20-deoxo-20-[(4,4-dioxothiomorpholinyl)-imino]-tylosin.

2′,4″-Di-O-acetyl-4‴-O-(tert-butyldimethylsilyl)-20-deoxo-20-[(4,4-dioxothiomorpholinyl)-imino]-tylosin (prepared as in part C of this Example) (2.3 g) and anhydrous tetra-n-butylammonium flouride (obtained by azeotroping the trihydrate (583 mg) with toluene) are dissolved in dry tetrahydrofuran (100 ml). The resulting solution is allowed to remain at 25° C. for 2 hours under dry argon gas. The solution is evaporated to dryness and the residue taken up in dichloromethane. The dichloromethane solution is washed with saturated aqueous sodium bicarbonate, water, dried (MgSO$_4$), filtered and evaporated to dryness. Chromatography of the residue on a silica gel column (60×2 cm) using 40% acetone in hexane as the eluant gives 2′,4″-di-O-acetyl-20-deoxo-20-[(4,4-dioxothiomorpholinyl)-imino]-tylosin as a colorless, amorphous solid, having: Rotation: $[\alpha]_D^{26}$ −71.6° (CHCl$_3$); UV: $\lambda_{max}$ (CF$_3$CH$_2$OH) 232 nm ($\epsilon$7,355), 286 nm ($\epsilon$22,958); IR: $\nu_{max}$ (CDCl$_3$) 3520, 2980, 2950, 2900, 1740, 1720, 1680, 1595, 1315, 1240, 1170, 1128, 1050 cm$^{-1}$; NMR: $\delta_H$ (CDCl$_3$) 1.79 (3H,d,J$_{13,22}$ 1.5 Hz, 22-CH$_3$), 2.08 (3H,s,2′-OCOCH$_3$), 2.17 (3H,s,4″-OCOCH$_3$), 2.43 (6H,s,3′-N(CH$_3$)$_2$), 3.50(3H,s,2‴-OCH$_3$), 3.63(3H,s,3‴-OCH$_3$), 5.96 (1H,dq,J$_{13,22}$ 1.5 Hz, J$_{13,14}$ 10 Hz, H$_{13}$), 6.12 (1H,d,J$_{10,11}$ 15.5 Hz, H$_{10}$), 7.00(1H,t,J$_{19,20}$ 5 Hz,H$_{20}$) and 7.40 (1H,d,J$_{10,11}$ 15.5 Hz, H$_{11}$).

E. 2′,4″-Di-O-acetyl-20-deoxo-20-[(4,4-dioxothiomorpholinyl)-imino]-4‴-oxo-tylosin.

Repetition of the procedure detailed in paragraph F of the foregoing Example 1 using 2′, 4″-di-O-acetyl-20-deoxo-20-[(4,4-dioxothiomorpholinyl)-imino]-tylosin in place of the 2′-O-acetyl-20-deoxo-20-[(4,4-dioxo-thiomorpholinyl)-imino]-4‴-O-iso-valeryltylosin affords the title product, 2′,4″-di-O-acetyl-20-deoxo-20-[(4,4-dioxothiomorpholinyl)-imino]-4‴-oxo-tylosin.

EXAMPLE 3

4″-O-Acetyl-23-O-demycinosyl-20-deoxo-20-[(4,4-dioxothiomorpholinyl)-imino]-tylosin.

Utilizing 2′,4″-di-O-acetyl-20-deoxo-20-[(4,4-dioxothiomorpholinyl)-imino]-4‴-oxo-tylosin in place of the 4‴-oxo-20-deoxy-20-[(4,4-dioxothiomorpholinyl)imino]-4″-O-iso-valeryltylosin utilized in paragraph G of the foregoing Example 1, and substantial reetition of the procedure detailed therein, affords the title compound, 4″-O-acetyl-23-O-demycinosyl-20-deoxo-20-[(4,4-dioxothiomorpholinyl)imino]-tylosin.

EXAMPLE 4

A. 20,2′,4″-Tri-O-acetyl-4‴-O-(tert-butyldimethylsilyl)-tylosin-3,20-hemiacetal.

4‴-O-(tert-Butyldimethylsilyl)-tylosin (prepared in part A of Example 1) (5.82 g.) and anhydrous potassium carbonate (5.82 g.) are treated with acetic anhydride (331 ml.) and the mixture heated under dry nitrogen gas at 60°-65° C. for 5 hours. The mixture is evaporated to dryness in vacuo and the residue azeotroped with toluene. The residue is then taken up in dichloromethane-water. The dichloromethane layer is washed with water, dried (MgSO$_4$), filtered and evaporated to dryness. Chromatography of the residue on a Waters Prep 500 HPLC instrument using one silica gel cartridge and 15% acetone in hexane as the eluant, gives 20,2′,4″-tri-O-acetyl-4‴-O-(tert-butyldimethylsilyl)-tylosin-3,20-hemiacetal as a colourless, amorphous solid, having: Rotation: $[\alpha]_D^{26}$−79.0° (CHCl$_3$); UV: $\lambda_{max}$ (CF$_3$CH$_2$OH) 282 nm ($\epsilon$24,707); IR $\nu_{max}$(CDCl$_3$) 3500, 2970, 2930, 2900, 1735, 1650, 1630, 1365, 1240, 1050 cm.$^{-1}$; NMR: $\delta_H$ (CDCl$_3$) 0.10 (3H,s,4″-SiCH$_3$), 0.12 (3H,s,4‴-SiCH$_3$), 0.93 (9H,s,4‴-SiC(CH$_3$)$_3$), 1.92 (3H,s,20-OCOCH$_3$), 1.92 (3H,d,J$_{13,22}$ 1.5 Hz, 22-CH$_3$), 2.08 (3H,s, 2′-OCOCH$_3$), 2.14 (3H,s,4″-OCOCH$_3$), 2.34 (6H,s,3′-N (CH$_3$)$_2$), 3.39 (3H,s,2‴-OCH$_3$), 3.56 (3H,s,3‴-OCH$_3$), 5.79 (1H,dd,J$_{19,20}$ 2 Hz,J$_{19,20}$ 8 Hz, H$_{20}$), 6.04 (1H,dq,J$_{13,22}$ 1.5 Hz, J$_{13,14}$ 10 Hz, H$_{13}$), 6.24(1H,d,J$_{10,11}$ 15.5Hz, H$_{10}$) and 7.00 (1H,d,J$_{10,11}$ 15.5 Hz, H$_{11}$).

B. 20,2′,4″-Tri-O-acetyltylosin-3,20-hemiacetal.

20,2′,4″-Tri-O-acetyl-4‴-O-(tert-butyldimethylsilyl)-tylosin-3,20-hemiacetal (prepared as in part A of this Example) (1.9 g.) is dissolved in anhydrous tetrahydrofuran (73 ml.) containing anhydrous tetra-n-butylammonium fluoride, (prepared by azeotroping the trihydrate (518 mg.) with toluene). The solution is allowed to stand under dry argon gas at 25° C. for 1 hour. The mixture is evaporated to dryness and the residue is taken up in dichloromethane and water. The pH is adjusted to 9.9 with aqueous sodium hydroxide. Then, the dichloromethane layer is washed with water, dried (MgSO$_4$), filtered and evaporated to dryness. Chromatography of the residue on a Waters Prep 500 HPLC instrument using one silica gel cartridge and 30% acetone in hexane as the eluant gives 20,2′,4″-tri-O-acetyltylosin-3,20-hemiacetal as a colorless, amorphous solid, having: Rotation: $[\alpha]_D^{26}$ −94.9° (CHCl$_3$); UV: $\lambda_{max}$ (CF$_3$CH$_2$OH) 281 nm ($\epsilon$27,097); IR: $\nu_{max}$(CDCl$_3$) 3560, 3500, 2980, 2940, 2890, 1740, 1655, 1373, 1240, 1050 cm.$^{-1}$; NMR: $\delta_H$ (CDCl$_3$) 0.89 (3H,t,J$_{16,17}$ 7 Hz, 17-CH$_3$), 0.99 (3H,d,J$_{4,18}$ 6 Hz, 18-CH$_3$) 1.11 (3H,d,J6 Hz,CH$_3$) 1.13 (3H,s,3″-CH$_3$), 1.16 (3H,d,J6 Hz,CH$_3$), 1.28 (6H,d,J 6 Hz, CH$_3$ and CH$_3$), 1.94 (3H,s, 20-OCOCH$_3$), 1.94 (3H, d, J$_{13,22}$ 1.5 Hz, 22-CH$_3$), 2.07 (3H,s,2′-OCOCH$_3$), 2.13 (3H,s,4″-OCOCH$_3$), 2.37 (6H,s,3′-N(CH$_3$)$_2$), 3.41 (3H,s,2‴-OCH$_3$), 3.58(3H,s,3‴-OCH$_3$), 5.83(1H,dd, J$_{19,20}$ 2.0 Hz, J$_{19′,20}$ 10 Hz,H$_{20}$), 6.07(1H, dq, J$_{13,22}$ 1.5 Hz, J$_{13,14}$ 10 Hz, H$_{13}$), 6.28 (1H,d,J$_{10,11}$ 16 Hz, H10) and 7.01 (1H,d, J$_{10,11}$ 16 Hz, H$_{11}$).

C. 20,2′,4″-Tri-O-acetyl-4‴-oxo-tylosin-3,20-hemiacetal.

20,2′,4″-Tri-O-acetyltylosin-3,20-hemiacetal (prepared as in part B of this example) (817 mg.) and dicyclohexylcarbodiimide (450 mg.) are dissolved in a 15% solution of dry dimethylsulphoxide in dry benzene 14.9 ml). Dry pyridine (49 mg.) and trifluoroacetic acid (33.5 mg) dissolved in a 15% solution of dry dimethylsulphoxide in dry benzene (3 ml.) is added and the mixture stirred under dry argon gas at 25° C. for 20 hours. Additional dicyclohexylcarbodiimide (450 mg.), dry pyridine (49 mg.) and trifluoroacetic acid (33.5 mg.) are added and the reaction is continued for a further 4 hours. The benzene is distilled off in vacuo and the residue is taken up in dichloromethane-water. The pH is then adjusted to 9.9 with aqueous sodium hydroxide. The dichloromethane layer is washed with water, dried (MgSO$_4$), filtered and evaporated to dryness. Chromatography of the residue on a silica gel column (30×3 cm.) using dichloromethane as the first eluant (1.5 l.), and then 10% acetone in hexane, gives the desired 20,2′,4″-tri-O-acetyl-4‴-oxo-tylosin-3,20-hemiacetal.

D. 23-O-Demycinosyltylosin.

The 20,2′,4″-tri-O-acetyl-4‴-oxo-tylosin-3,20-hemiacetal (prepared in paragraph C of this Example) is dissolved in methanol (10 ml.) and a 2.8% (w/w) solution of sodium methoxide in methanol (0.25 ml) is added. The mixture is allowed to stand under argon at 25° C.

for 35 minutes. The solution is then evaporated to dryness and the residue taken up in dichloromethane-water. The dichloromethane layer is washed with water, dried (MgSO$_4$), filtered and evaporated to dryness. The residue is taken up in methanol (35 ml) containing triethylamine (2.5 ml.) and the solution is heated under reflux at 60° C. for 20 hours. The solution is then evaporated to dryness and the residue chromatographed on a silica gel columnm (30×5 cm.) using 20% increasing to 30% acetone in hexane as the eluant to give 23-O-demycinosytylosin as a colorless amorphous solid, having: Rotation: $[\alpha]_D^{26}$ −41.9° (CHCl$_3$); UV: $\lambda_{max}$ (CF$_3$CH$_2$OH) 284 nm ($\epsilon$18,236), IR: $\nu_{max}$(CDCl$_3$)3490, 2980, 2940, 2900, 1720, 1680, 1595, 1250, 1188, 1165, 1050 cm.$^{-1}$; NMR: $\delta_H$ (CDCl$_3$) 0.95 (3H,t,J$_{16,17}$ 7 Hz, 17-CH$_3$), 1.00 (3H,d,J$_{4,18}$ 6 Hz, 18-CH$_3$), 1.83(3H,d,J$_{13,22}$ 1.5 Hz, 22-CH$_3$), 2.50(6H,s,3'-N(CH$_3$)$_2$), 4.24 (1H,d,J$_{1',2'}$ 7 Hz, H$_{1'}$), 5.92 (1H,dq,J$_{13,22}$ 1.5 Hz, J$_{13,14}$ 10 Hz, H$_{13}$), 6.31(1H,d,J$_{10,11}$ 15 Hz, H$_{10}$), 7.36 (1H,d, J$_{10,11}$ 15 Hz,H$_{11}$) and 9.70(1H,s,H$_{20}$).

E. Demycinosyloxy-23-iodotylosin.

23-O-Demycinosyltylosin (prepared as in paragraph D of this Example) (5 g.) is dissolved in dry dimethylformamide (100 ml.). Methyl triphenoxyphosphonium iodide (6.1 g, freshly washed with ethyl acetate) dissolved in dry dimethylformamide (250 ml) is added dropwise, with stirring, at 25° C. over a period of 2 hours. The mixture is stirred for an additional 2.5 hours and then quenched with methanol (50 ml). The solution is evaporated to dryness and the residue taken up in a chloroform-water mixture. The chloroform layer is washed first with dilute aqueous sodium thiosulfate, and then with water, dried (MgSO$_4$), filtered and evaporated to dryness. The residue is chromatographed on a silica gel column (120×5 cm) using 4% methanol in chloroform as the eluant to afford the title product, 23-demycinosyloxy-23-iodotylosin.

F. Substantial repetition of the procedures detailed in paragraphs B through E of Example 1 using 23-demycinosyloxy-23-iodotylosin (prepared as in paragraph E of this Example) affords 2'-O-acetyl-20-deoxo-20-[(4,4-dioxothiomorpholininyl)imino]-4"-O-isovaleryl-23-demycinosyloxy-23-iodotylosin.

EXAMPLE 5

A. 23-O-(tert-Butyldimethylsilyl)-23-O-demycinosyltylosin.

23-O-Demycinosyltylosin (prepared as in paragraph D of Example 4) (20 g.) and imidazole (3.7 g.) are dissolved in dry dimethylformamide (200 ml). A solution of tert-butyldimethylsilyl chloride (4.1 g.) in dry dimethylformamide (100 ml.) is added dropwise over 2 hours and the mixture is stirred at 25° C. for an additional 16 hours. The reaction is worked up and the product purified as in Example 1 paragraph A to give 23-O-(tert-butyldimethylsilyl)-23-O-demycinosyltylosin.

B. 2'-O-Acetyl-23-O-(tert-butyldimethylsilyl)-23-O-demycinosyltylosin.

23-O-(tert-Butyldimethylsilyl)-23-O-demycinosyltylosin (prepared as in paragraph A of this example) (10 g.) is treated with acetic anhydride (4.8 g.) in dry acetone (100 ml.) in essentially the same manner as described in paragraph B of Example 1, to afford 2'-O-acetyl-23-O-(tert-butyldimethylsilyl)-23-O-demycinosyltylosin.

C. 2',4"-Di-O-acetyl-23-O-(tert-butyldimethylsilyl)-23-O-demycinosyltylosin.

2'-O-Acetyl-23-O-(tert-butyldimethylsilyl)-23-O-demycinosyltylosin (prepared as in paragraph B of this example) (8 g.) and 4-dimethylaminopyridine (1.1 g.) and triethylamine (10 ml.) are dissolved in dry dichloromethane (100 ml.). Acetic anhydride (0.9 g.) in dry dichloromethane (50 ml.) is added as described in paragraph C of Example 1 and the reaction is worked up and the product is purified as described in Example 1 to give 2',4"-di-O-23-O-(tert-butyldimethylsilyl)-23-O-demycinosyltylosin.

D. 2',4"-Di-O-acetyl-23-O-demycinosyltylosin.

2',4"-Di-O-acetyl-23-O-(tert-butyldimethylsilyl)-23-O-demycinosyltylosin (prepared as in paragraph C of this example) (5 g.) is dissolved in 80% acetic acid-water (50 ml.) and the solution is allowed to remain at 25° C. for 2 hours. The pH is adjusted to 9.5 with dilute aqueous sodium carbonate the the aqueous layer is extracted with dichloromethane. The latter is washed with water, dried (MgSO$_4$), filtered and evaporated to dryness. The product is chromatographed on a preparative HPLC instrument using a silica gel cartridge and 20% acetone in hexane as the eluant of give 2',4"-di-O-acetyl-23-O-demycinosyltylosin.

E. 4"-O-Acetyl-23-O-demycinosyltylosin.

2',4"-Di-O-acetyl-23-O-demycinosyltylosin (prepared as in paragraph D of this example) (3 g.) is dissolved in methanol (100 ml.) and the solution is allowed to remain at 25° C. for 94 hours. The solution is evaporated to dryness and the product is chromatographed on a preparative HPLC instrument using a silica gel cartridge and 20% acetone in hexane as the eluant to give 4"-O-acetyl-23-O-demycinosyltylosin.

F. 4"-O-Acetyl-23-O-demycinosyl-20-deoxo-20-[(4,4-dioxothiomorpholinyl)-imino]tylosin.

4"-O-Acetyl-23-O-demycinosyltylosin (prepared as in paragraph E of this example) (2 g.) and 1-N-amino-4,4-dioxothiomorpholine (383 mg.) are dissolved in dry dichloromethane (50 ml.) and the mixture is stirred at 25° C. for 72 hours. The solution is evaporated to dryness and the residue is chromatographed on a preparative HPLC instrument using a silica gel cartridge and 30% acetone in hexane is the eluant to give 4"-O-acetyl-23-O-demycinosyl-20-deoxo-20-[(4,4-dioxothiomorpholinyl)imino]-tylosin.

EXAMPLE 6

A. 3,2',4"-Tri-O-acetyl-23-O-(tert-butyldimethylsilyl)-23-O-demycinosyltylosin.

2',4"-Di-O-acetyl-23-O-(tert-butyldimethylsilyl)-23-O-demycinosyltylosin (prepared as in paragraph C of Example 5) (5 g.), 4-dimethylaminopyridine (3.25 g.) and triethylamine (5 ml.) are dissolved in dry dichloromethane (100 ml.). Acetic anhydride (2.7 g.) is added and the mixture is allowed to remain at 25° C. for 16 hours. The reaction is worked up and purified as described in paragraph C of Example 1 to afford 3,2',4"-tri-O-acetyl-23-O-(tert-butyldimethylsilyl)-23-O-demycinosyltylosin.

B. 3,2',4"-Tri-O-acetyl-23-O-demycinosyltylosin.

3,2',4"-Tri-O-acetyl-23-O-(tert-butyldimethylsilyl)-23-O-demycinosyltylosin (prepared as in paragraph A of this example) (3 g.) is dissolved in 80% acetic acid-water (50 ml.) and the reaction is carried out and the product purified as described in paragraph D of Example 5, to give 3,2',4"-tri-O-acetyl-23-O-demycinosyltylosin.

C. 3,4"-Di-O-acetyl-23-O-demycinosyltylosin.

3,2',4''-Tri-O-acetyl-23-O-demycinosyltylosin (prepared as in paragraph B of this example) (2 g.) is dissolved in methanol (50 ml.) and the reaction is carried out and the product purified as in paragraph E of Example 5, to give 3,4''-di-O-acetyl-23-O-demycinosyltylosin.

D. 3,4''-Di-O-acetyl-23-O-demycinosyl-20-deoxo-20-[(4,4-dioxothiomorpholinyl)-imino]-tylosin.

3,4''-Di-O-acetyl-23-O-demycinosyltylosin (prepared as in paragraph C of this example) (1 g.) and 1-N-amino-4,4-dioxothiomorpholine (160 mg.) are dissolved in dry dichloromethane (50 ml.) and the reaction is carried out and the product purified as described in paragraph F of Example 5, to give 3,4''-di-O-acetyl-23-O-demycinosyl-20-deoxo-20-[(4,4-dioxothiomorpholinyl)-imino]-tylosin.

EXAMPLE 7

3,2',4''-Tri-O-acetyl-23-O-demycinosyl-20-deoxo-20-[(4,4-dioxothiomorpholinyl)-imino]-tylosin 3,2'4''-Tri-O-acetyl-23-O-demycinosyltylosin (prepared as in paragraph B of Example 6) (1 g.) and 1-N-amino-4,4-dioxothiomorpholine (173 mg.) are dissolved in dry dichloromethane (50 ml.) and the reaction is carried out and the product purified as in paragraph F of Example 5, to give 3,2'4''-tri-O-acetyl-23-O-demycinosyl-20-deoxo-20-[(4,4-dioxothiomorpholinyl)-imino]-tylosin.

EXAMPLE 8

A. 2',3''-Di-O-acetyl-23-O-(tert-butyldimethylsilyl)-23-O-demycinosyl-4''-O-iso-valeryltylosin 2'-O-Acetyl-23-O-(tert-butyldimethylsilyl)-23-O-demycinosyl-4''-O-iso-valeryltylosin (prepared as in paragraph B of Example 5 and as in paragraph C of Example 5 using iso-valeric anhydride in place of acetic anhydride) (10 g.) is dissolved in dry 1,2-dichloroethane (200 ml.) and tribenzylamine (4.4 g.) and trimethylsilyl chloride (1.3 g.) are added. The solution is allowed to remain at 5° C. for 16 hours. The solution is poured into water and the pH is adjusted to 9.5 with aqueous sodium bicarbonate. The dichloroethane is then washed with water, dried (MgSO$_4$), filtered and evaporated to dryness to give 2',3''-di-O-acetyl-23-O-(tert-butyldimethylsilyl)-23-O-demycinosyl-3-trimethylsilyl-4''-O-iso-valeryltylosin. The product is taken up in dry 1,2-dichloroethane (200 ml.) and tribenzylamine (35.1 g.) and acetyl chloride (8.0 g.) are added. The mixture is heated at 70° C. under reflux for 20 hours. Water is added and the pH is adjusted to 9.5 with aqueous sodium bicarbonate. The dichlorethane is washed with water, dried (MgSO$_4$), filtered and evaporated to dryness. The residue is dissolved in methanol (500 ml.) and 8% aqueous potassium carbonate (50 ml.) and the mixture is stirred at 25° C. for 1 hour. The pH is adjusted to 7.0 with acetic acid and the solution is evaporated to dryness. The residue is taken up in dichloromethane water and the pH is adjusted to 9.5. The dichloromethane layer is washed with water, dried (MgSO$_4$), filtered and evaporated to dryness. The residue is chromatographed on a preparation HPLC instrument using two silica gel cartridges and 25% acetone in hexane as the eluant to give 2',3''-di-O-acetyl-23-O-(tert-butyldimethylsilyl)-23-O-demycinosyl-4''-O-iso-valeryltylosin.

B. 2',3''-Di-O-acetyl-23-O-demycinosyl-4''-O-isovaleryltylosin.

2',3''-Di-O-acetyl-23-O-(tert-butyldimethylsilyl)-23-O-demycinosyl-4''-O-iso-valeryltylosin (prepared as in paragraph A of this example) (5 g.) is dissolved in 80% aqueous acetic acid (100 ml.) and reaction is carried out essentially as described in paragraph D of Example 5, to afford 2',3''-di-O-acetyl-23-O-demycinosyl-4''-O-iso-valeryltylosin.

C. 3''-O-Acetyl-23-O-demycinosyl-4''-O-iso-valeryltylosin.

2'3''-Di-O-acetyl-23-O-demycinosyl-4''-O-iso-valeryltylosin (prepared as in paragraph B of this example) (3 g.) is dissolved in methanol (50 ml.) and the reaction is conducted substantially as described in paragraph E of Example 5, to give 3''-O-acetyl-23-O-demycinosyl-4''-O-iso-valeryltylosin.

D. 3''-O-Acetyl-23-O-demycinosyl-20-deoxo-20-[(4,4-dioxothiomorpholinyl)-imino]-4''-O-iso-valeryltylosin. 3''-O-Acetyl-23-O-demycinosyl-4''-O-iso-valeryltylosin (prepared as in paragraph C of Example 11) (2 g.) and 1-N-amino-4,4-dioxothiomorpholine (346 mg.) are dissolved in dry dichloromethane (50 ml.) an the reaction is carried out substantially as described in paragraph F of Example 5, to give 3''-O-acetyl-23-O-demycinosyl-20-deoxo-20-[(4,4-dioxothiomorpholinyl)-imino]-4''-O-iso-valeryltylosin.

EXAMPLE 9

A. 3,2'-Di-O-acetyl-23-O-(tert-butyldimethylsilyl)-23-O-demycinosyl-4''-O-iso-valeryltylosin.

2'-O-Acetyl-23-O-(tert-butyldimethylsilyl)-23-O-demycinosyl-4''-O-iso-valeryltylosin (prepared as in paragraph B of Example 5 and as in paragraph C of Example 5 using iso-valeric anhydride in the latter case) (10 g.), 4-dimethylaminopyridine (6.2 g.) and triethylamine (10 ml.) are dissolved in dry dichloromethane (200 ml.). Acetic anhydride (5.2 g.) is added and the mixture is allowed to remain at 25° C. for 16 hours. The reaction is worked up and purified as described in paragraph C of Example 1, to give 3,2'-di-O-acetyl-23-O-(tert-butyldimethylsilyl)-23-O-demycinosyl-4''-O-iso-valeryltylosin.

B. 3,2',3''-Tri-O-acetyl-23-O-(tert-butyldimethylsilyl)-23-O-demycinosyl-4''-O-iso-valeryltylosin.

3,2'-Di-O-acetyl-23-O-(tert-butyldimethylsilyl)-23-O-demycinosyl-4''-O-iso-valeryltylosin (prepared as in paragraph A of this example) (5 g.) is dissolved in dry 1,2-dichloroethane (100 ml.) and tribenzylamine (16.8 g.) and acetyl chloride (3.8 g.) are added. The mixture is heated at 70° C. under reflux for 20 hours. Water is added and the pH is adjusted to 9.5 with aqueous sodium bicarbonate. The dichloroethane is washed with water, dried (MgSO$_4$), filtered and evaporated to dryness to give 3,2',3''-tri-O-acetyl-23-O-(tert-butyldimethylsilyl)-23-O-demycinosyl-4''-O-iso-valeryltylosin.

C. 3,2',3''-Tri-O-acetyl-23-O-demycinosyl-4''-O-iso-valeryltylosin.

3,2',3''-Tri-O-acetyl-23-O-(tert-butyldimethylsilyl)-23-O-demycinosyl-4''-O-iso-valeryltylosin (prepared as in paragraph B of this example) (3 g.) is dissolved in 80% aqueous acetic acid (50 ml.) and the reaction is carried out and product purified as in paragraph D of Example 5, to give 3,2',3''-tri-O-acetyl-23-O-demycinosyl-4''-O-iso-valeryltylosin.

D. 3,3''-Di-O-acetyl-23-O-demycinosyl-4''-O-iso-valeryltylosin.

3,2',3''-Tri-O-acetyl-23-O-demycinosyl-4''-O-iso-valeryl-tylosin (prepared as in paragraph C of this example) (2 g.) is dissolved in methanol (50 ml.) and the reaction is now as described in paragraph E of Example 5, to give 3,3''-di-O-acetyl-23-O-demycinosyl-4'''-O-isovaleryltylosin.

E. 3,3''-Di-O-acetyl-23-O-demycinosyl-20-deoxo-20-[(4,4-dioxothiomorpholinyl)-imino]-4'''-O-iso-valeryltylosin.

3,3''-Di-O-acetyl-23-O-demycinosyl-4'''-O-isovaleryltylosin (prepared as in paragraph D of this example) (1 g.) and 1-N-amino-4,4-dioxothiomorpholine (165 mg.) are dissolved in dry dichloromethane (50 ml.) and the reaction is carried out as described in paragraph E of Example 5, to give 3,3''-di-O-acetyl-23-O-demycinosyl-20-deoxo-20-[(4,4-dioxothiomorpholinyl)-imino]-4'''-O-iso-valeryltylosin.

EXAMPLE 10

A. 3,2',4''-Tri-O-acetyl-23-O-demycinosyl-20-deoxo-20-[(4,4-dioxothiomorpholinyl)-imino]-23-oxotylosin.

3,2',4''-Tri-O-acetyl-23-O-demycinosyl-20-deoxo-20-[(4,4-dioxothiomorpholinyl)-imino]-tylosin (prepared as in paragraph E of Example 6) (1 g.) and dicyclohexylcarbodiimide (619 mg.) are dissolved in a mixture of dry dimethylsulphoxide (3 ml.) and dry benzene (20 ml.). Pyridine (79 mg.) and trifluoroacetic acid (57 mg.) are added and the mixture is stirred at 25° C. for 5 hours. The benzene is evaporated off in vacuo and the residue is taken up in dichloromethane and washed with water. The dichloromethane layer is dried (MgSO4), filtered and evaporated to dryness. The residue is chromatographed on a preparative HPLC instrument using a silica gel cartridge and 25% acetone in hexane as the eluant to give 3,2',4''-tri-O-acetyl-23-O-demycinosyl-20-deoxo-20-[(4,4-dioxothiomorpholinyl)imino]-20-oxotylosin.

EXAMPLE 11

3,4''-Di-O-acetyl-23-O-demycinosyl-20-deoxo-20-[(4,4-dioxothiomorpholinyl)-imino]-23-oxotylosin 3,2',4''-Tri-O-acetyl-23-O-demycinosyl-20-deoxo-20-[(4,4-dioxothiomorpholinyl)-imino]-23-oxotylosin (prepared as in paragraph A of Example 10) (2 g.) is dissolved in methanol (50 ml.) and the reaction is carried out substantially as described in paragraph E of Example 9, to give 3,4''-di-O-acetyl-23-O-demycinosyl-20-deoxo-20-[(4,4-dioxothiomorpholinyl)-imino]-23-oxotylosin.

EXAMPLE 12

3,4''-Di-O-acetyl-23-O-demycinosyl-20,23-dideoxo-20,23-di-[(4,4-dioxothiomorpholinyl)-imino]-tylosin 3,4''-Di-O-acetyl-23-O-demycinosyl-20-deoxo-20-[(4,4-dioxothiomorpholinyl)-imino]-23-oxotylosin (prepared as in Example 11) (1 g.) and 1-N-amino-4,4-dioxothiomorpholine (138 mg.) are dissolved in dry dichloromethane (50 ml.) and the reaction is carried out and the product isolated substantially as described in paragraph F of Example 9, to give 3,4''-di-O-acetyl-23-O-demycinosyl-20,23-dideoxo-20,23-di-[(4,4-dioxothiomorpholinyl)-imino]-tylosin.

EXAMPLE 13

A. 23-Fluoro-23-demycinosyloxytylosin.

23-O-Demycinosyltylosin (prepared as in paragraph D of Example 3) (1.5 g.) and triphenyldifluorophosphorane (979 mg.) are dissolved in dry acetonitrile (20 ml.) and the mixture is heated at 150° C. in a sealed bomb for 10 hours. After cooling, the solution is diluted with dichloromethane and then washed first with saturated aqueous sodium bicarbonate, then with water, dried (MgSO4), filtered and evaporated to dryness. The residue is chromotographed on a silica gel column (110×2.5 cm.) using 3% methanol in chloroform as the eluant to give 23-fluoro-23-demycinosyloxytylosin.

B. Substantial repetition of the procedures detailed in paragraphs B through E of Example 1 using 23-fluoro-23-demycinosyloxytylosin (prepared as in paragraph A of this example) affords 2'-O-acetyl-20-deoxo-20-[(4,4-dioxothiomorpholinyl)-imino]-4'''-O-isovaleryl-23-demycinosyloxy-23-fluorotylosin.

EXAMPLE 14

A. 23-Chloro-23-demycinosyloxytylosin.

23-Demycinosyloxytylosin (prepared as in paragraph D of Example 3) (1.5 g.) and carbon tetrachloride (623 mg.) are dissolved in dry dimethylformamide (100 ml.). Tris(dimethylamino)-phosphorous amide (527 mg.) dissolved in dry dimethylformamide (25 ml.) is added to the stirred solution at −45° C. and the stirring is continued for 1 hour. The solution is allowed to warm up to 25° C. and is then heated at 80° C. under reflux for 20 hours. The mixture is evaporated to dryness and the residue taken up in chloroform, washed with water, dried (MgSO4) and evaporated to dryness. The residue is chromatographed on a silica gel column (110×2.5 cm) using 3% methanol in chloroform as the eluant to give 23-chloro-23-demycinosyloxytylosin.

B. Substantial repetition of the procedure detailed in paragraphs B through E of Example 1 using 23-chloro-23-demycinosyloxytylosin (prepared as in paragraph A of this Example) affords 2'-O-acetyl-20-deoxo-20-[(4,4-dioxothiomorpholinyl)imino]-4'''-O-isovaleryl-23-chloro-23-demycinosyloxytylosin.

EXAMPLE 15

A. 23-Bromo-23-demycinosyloxytylosin.

23-Demycinosyloxytylosin (prepared as in paragraph D of Example 3) (1.5 g.) and carbon tetrabromide (1.34 g.) are dissolved in dry dimethylformamide (100 ml.). Tris(dimethylamino)-phosphorous amide (527 mg.) in dry dimethylformamide (25 ml.) is added to the stirred solution at −45° C. and the stirring is continued for 1 hour. The solution is allowed to warm up to 25° C. and then is heated at 80° C. under reflux for 20 hours. The solution is evaporated to dryness and the residue solution is evaporated to dryness and the residue taken up in chloroform, washed with water, dried (MgSO4), filtered and evaporated to dryness. The residue is then chromatographed on a silica gel column (110×2.5 cm.) using 3% methanol in chloroform as the eluant to give 23-bromo-23-demycinosyloxytylosin.

EXAMPLE 16

A. 23-Demycinosyloxytylosin.

23-Demycinosyloxy-23-iodotylosin (prepared as in Example 4) (1 g.) is dissolved in dry tetrahydrofuran (150 ml.) and the mixture maintained under dry argon. Freshly distilled tri-n-butyltinhydride (10 ml.) is added and the mixture stirred at 60° C. for 70 hours. The solution is evaporated to dryness and the residue chromatography on a silica gel column (30×5 cm) using 2% methanol in chloroform as the eluant to give the title product, 23-demycinosyloxytylosin.

B. Substantially repeating the procedures detailed in paragraphs B through E of Example 1 using 23-demycinosyloxytylosin (prepared as in paragraph A of this example) affords 2'-O-acetyl-20-deoxo-20[(4,4-dioxothiomorpholinyl)imino]-4″-O-isovaleryl-23-demycinosyloxytylosin.

EXAMPLE 17

A. 2′,23-Di-O-acetyl-23-O-demycinosyltylosin.

23-O-Demycinosyltylosin (prepared as in paragraph D of Example 3) (10 g.) and acetic anhydride (2.8 g.) are dissolved in dry pyridine (100 ml.) and the solution is allowed to remain at 25° C. for 20 hours. The reaction is worked up substantially as described in paragraph B of Example 1 to give 2′,23-di-O-acetyl-23-O-demycinosyltylosin.

B. Substantial repetition of the procedures detailed in paragraphs B through F of Example 1 using 2′,23-di-O-acetyl-23-O-demycinosyltylosin (prepared as in paragraph A of this example) affords 2′,23-di-O-acetyl-20-deoxo-20-[(4,4-dioxothiomorpholinyl)imino]-4″-O-isovaleryl-23-demycinosyltylosin.

EXAMPLE 18

A. 23-O-Demycinosyl-20-deoxo-20-[(4,4-dioxothiomorpholinyl)-imino]-tylosin.

23-O-Demycinosyltylosin (prepared as in paragraph D of Example 3) (10 g.) and 1-N-amino-4,4-dioxothiomorpholine (20 g.) are dissolved in methanol (100 ml.) and the reaction is run as described in paragraph F of Example 5, to give 23-O-demycinosyl-20-deoxo-20-[(4,4-dioxothiomorpholinyl)-imino]-tylosin.

B. 23-Iodo-23-demycinosyloxy-20-deoxo-20-[(4,4-dioxothiomorpholinyl)-imino]-tylosin.

23-O-Demycinosyloxy-20-deoxo-20-[(4,4-dioxothiomorpholinyl)-imino]-tylosin (prepared as in paragraph A of this example) (5 g.) is reacted with methyl triphenoxyphosphonium iodide (5.2 g.) in dry dimethylformamide (500 ml.) as described in Example 4, to give 23-iodo-23-demycinosyl-20-deoxo-20-[(4,4-dioxothiomorpholinyl)-imino]-tylosin.

C. 23-(Di-N-ethylamino)-23-demycinosyloxy-20-deoxo-20-[(4,4-dioxothiomorpholinyl)-imino]-tylosin.

23-Iodo-23-demycinosyl-20-dioxo-20-[(4,4-dioxothiomorpholinyl)-imino]-tylosin (prepared as described in paragraph B of this example) (2 g.) and diethylamine (2.8 g.) are dissolved in dry acetonitrile (40 ml.) and the mixture is heated at 80° C. in a sealed tube for 1 hour. The solution is evaporated to dryness and the residue is chromatographed on a silica gel column (110×2.5 cm) using 30% acetone in hexane as the elutant to give 23-(di-N-ethylamino)-23-demycinosyloxy-20-deoxo-20-[(4,4-dioxothiomorpholinyl)imino]-tylosin.

D. Substantial repetition of paragraphs B through E of Example 1 using 23-(di-N-ethylamino)-23-demycinosyloxy-20-deoxo-20-[(4,4-dioxothiomorpholinyl)imino]tylosin (prepared as in paragraph C of this example) affords 2′-O-acetyl-23-(di-N-ethylamino)-23-demycinosyloxy-20-deoxo-20 -[(4,4-dioxothiomorpholinyl)imino]-4″-O-isovaleryltylosin.

EXAMPLE 19

A. 2′-O-Acetyl-4‴-O-(tert-butyldimethylsilyl)-20-deoxo-20-[(4,4-dioxothiomorpholinyl)-imino]-tylosin.

4‴-O-(tert-Butyldimethylsilyl)-20-deoxo-20-[(4,4-dioxothiomorpholinyl)-imino]-tylosin (prepared as in paragraph B of Example 2) (1.41 g.) is dissolved in dry acetone (30 ml.) and acetic anhydride (0.5 ml.) is added. The mixture is allowed to remain at 25° C. for 40 hours. The solution is evaporated to dryness and the residue azetroped with toluene. The residue is taken up in a mixture of dichloromethane-water and the pH adjusted to 9.5 with dilute aqueous sodium hydroxide. The dichloromethane layer is washed with water, dried (MgSO$_4$), filtered and evaporated to dryness to give 2′-O-acetyl-4‴-O-(tert-butyldimethylsilyl)-20-deoxo-20-[(4,4-dioxothiomorpholinyl)-imino]-tylosin, as a colorless, amorphous solid. An analytical sample (200 mg.), prepared by chromatography on a silica gel column (60×2 cm.) using 30% acetone in hexane as the eluant, has: Rotation: $[\alpha]_D^{26}$ −52.2° (CHCl$_3$); UV: $\lambda_{max}$(CF$_3$C-H$_2$OH) 234 nm ($\epsilon$6,369), 286 nm ($\epsilon$22,441), IR:$\nu_{max}$ (CDCl$_3$) 3500, 2975, 2950, 2900, 1750, 1715, 1680, 1598, 1318, 1240, 1130, 1055, cm$^{-1}$; NMR: $\delta_H$ (CDCl$_3$) 0.09 (3H,s,4‴-SiC(CH$_3$)$_3$), 0.12(3H,s,4‴-SiCH$_3$), 0.92(9H,s,4‴-SiC(CH$_3$)$_3$), 1.77(3H,d,J$_{13,22}$ 1.5 Hz,22-CH$_3$), 2.07 (3H,s,2′-OCOCH$_3$), 2.40 (6H,s,3′-N(CH$_3$)$_2$), 3.49(3H,s,2‴-OCH$_3$), 3.61 (3H,s,3‴-OCH$_3$), 4.34 (1H,d,J$_{1',2'}$ 8 Hz,H$_{1'}$), 4.62 (1H,d,J$_{1''',2'''}$ 8 Hz,H$_{1'''}$), 5.96 (1H,dq, J$_{13,22}$ 1.5 Hz,J$_{13,14}$ 10.5 Hz, H$_{13}$), 6.31 (1H, d,J$_{10,11}$ 15 Hz, H$_{10}$), 6.99(1H,t,J$_{19,20}$ 5 Hz, H$_{20}$) and 7.38 (1H,d,J$_{10,11}$ 15 Hz, H$_{11}$).

B. 2′-O-Acetyl-4‴-O-(tert-butyldimethylsilyl)-3″,4″-O-carbonyl-20-deoxo-20-[(4,4-dioxothiomorpholinyl)imino]-tylosin.

2′-O-Acetyl-4‴-O-(tert-butyldimethylsilyl)-20-deoxo-20-[(4,4-dioxothiomorpholinyl)-imino]-tylosin (prepared as in paragraph A of this example) (1.2 g.) is dissolved in dry dichloromethane (50 ml.) and N,N′-carbonyldiimidazole (178 mg.) is added. The mixture is stirred at 25° C. for 20 hours. The solution is evaporated to dryness and the residue chromatographed on a silica gel column (200 g.) using 15% acetone in dichloromethane as the eluant to give 2′-O-acetyl-4‴-O-(tert-butyldimethylsilyl)-3″,4″-O-carbonyl-20-deoxo-20-[(4,4-dioxothiomorpholinyl)-imino]-tylosin as a colorless, amorphous solid, having: Rotation: $[\alpha]_D^{26}$ −46.3° C. (CHCl$_3$): UV: $\lambda_{max}$ (CH$_3$OH) 283 nm ($\epsilon$20,900); NMR: $\delta_H$ (CDCl$_3$) 0.10 (3H,s,4‴-SiCH$_3$), 0.14 (3H,s,4‴-SiCH$_3$), 0.93 (9Hs,4‴-SiC(CH$_3$)$_3$), 1.52 (3H,s,3″-CH$_3$), 1.77 (3H,d,J$_{13,22}$ 1.5 Hz, 22-CH$_3$), 2.00 (3H,s,2′-OCOCH$_3$), 2.40 (6H,s,3′-N(CH$_3$)$_2$), 3.48 (3H,s,2‴-OCH$_3$), 3.61 (3H,s,3‴-OCH$_3$), 4.60 (1H,d,J$_{1'',2''}$ 8 Hz, H$_{1''}$), 5.91 (1H,dq,J$_{13,22}$ 1.5 Hz, J$_{13,14}$ 10 Hz, H$_{13}$) 6.24 (1H,d,J$_{10,11}$ 15 Hz, H$_{10}$), 6.94 (1H,t,J$_{19,20}$ 5 Hz, H$_{20}$) and 7.32 (1H,d,J$_{10,11}$ 15 Hz, H$_{11}$).

C. 2′-O-Acetyl-3″,4″-O-carbonyl-20-deoxo-20-[(4,4-dioxothiomorpholinyl)-imino]-tylosin.

2′-O-Acetyl-4‴-O-(tert-butyldimethylsilyl)-3″,4″-O-carbonyl-20-deoxo-20-[(4,4-dioxothiomorpholinyl)-imino]-tylosin (prepared as in paragraph B of this example) (1.05 g.) is dissolved in anhydrous tetrahydrofuran (25 ml.) and tetra-n-butylammonium fluoride trihydrate (0.32 g.) is added. The mixture is stirred at 25° C. for 5 hours. The solution is evaporated to dryness and the residue taken up in dichloromethane-water. The dichloromethane layer is washed with water, dried (MgSO$_4$), filtered and evaporated to dryness. Chromatography of the residue on a silica gel column (100 g.) using 75% acetone in dichloromethane gives 2′-O-acetyl-3″,4″-O-carbonyl-20-deoxo-20-[(4,4-dioxothiomorpholinyl)-imino]-tylosin as a colorless, amorphous solid, having: Rotation: $[\alpha]_D^{26}$ −54.7° C. (CHCl$_3$); UV: $\lambda_{max}$ (CH$_3$OH) 280 nm ($\epsilon$11,100); NMR: $\delta_H$ (CD$_3$COCD$_3$), 1.56 (3H,s,3″-CH$_3$), 1.86 (3H,d,J$_{13,22}$ 1.5 Hz, 22-CH$_3$), 2.01 (3H,s,2′-OCOCH$_3$), 2.44 (6H,s,3′-N(CH$_3$)$_2$), 3.47 (3H,s,2‴-OCH$_3$), 3.53 (3H,s,3‴-OCH$_3$), 5.90 (1H,dq,J$_{13,22}$ 1.5 Hz, J$_{13,14}$ 10 Hz, H$_{13}$), 6.54 (1H,d,J$_{10,11}$ 15 Hz, H$_{10}$), 7.04 (1H,t,J$_{19,20}$ 5 Hz, H$_{20}$) and 7.25 (1H,d,J$_{10,11}$ 15 Hz, H$_{11}$).

D. 2'-Acetyl-4''''-oxo-3'',4''-carbonyl-20-deoxo-20-[(4,4-dioxothiomorpholinyl)imino]tylosin.

A solution of 2'-acetyl-3'',4''-O-carbonyl-20-deoxo-20-[(4,4-dioxothiomorpholinyl)imino]tylosin (558 mg.) in 2 ml. of dry DMSO (dimethyl sulfoxide) and 4 ml. of dry benzene is treated at room temperature with anhydrous pyridide (0.04 ml.), freshly distilled trifluoroacetic acid (0.02 ml.) and dicyclohexylcarbodimide (310 mg.). The mixture is stirred under N$_2$ for 4 hours and the solids are removed by filtration, washed with more benzene. The organic filtrate is washed three times with distilled water (3×5 ml.), once with saturated brine and dried (MgSO$_4$). Removal of solvent affords the title compound which was used for the next step without further purification.

E. 23-Demycinosyl-3'',4''-O-carbonyl-20-deoxo-20-[(4,4-dioxothiomorpholinyl)imino]tylosin.

The oxidation product obtained in paragraph D is dissolved in 10 ml. of methanol and the solution is treated with silica gel (5 g.). The mixture is stirred at room temperature for 4 days. Silica gel is removed by filtration and washed well with 5% methanol in CHCl$_3$; the combined filtrates are evaporated to dryness and the residue is purified on 100 g. silica gel column. Elution with 5% methanol in CHCl$_3$ gives 23-demycinosyl-3'',4''-O-carbonyl-20-deoxo-20-[(4,4-dioxothiomorpholinyl)imino]tylosin.

F. 2'-Acetyl-3'',4''-O-carbonyl-23-demycinosyl-20-deoxo-20-[(4,4-dioxothiomorpholinyl)imino]tylosin.

A solution of 3'',4''-O-carbonyl-23-demycinosyl-20-deoxo-20-[(4,4-dioxothiomorpholinyl)imino]tylosin (100 mg.) and acetic anhydride in dry methylene chloride (5 ml.) is stirred at room temperature overnight. Azeotropic distillation of the reaction mixture with benzene affords 2'-Acetyl-3'',4''-O-carbonyl-23-demycinosyl-20-deoxo-20-[(4,4-dioxothiomorpholinyl)imino]tylosin.

EXAMPLE 20

A. 23-O-(tert-Butyldimethylsilyl)-3'',4''-carbonyl-20-deoxo-20-[(4,4-dioxothiomorpholinyl)imino]-23-demycinosyltylosin.

Substantial repetition of the procedure detailed in paragraph A of Example 1 using 3'',4''-carbonyl-20-deoxo-20-[(4,4-dioxothiomorpholinyl)imino]-23-demycinosyltylosin (prepared as in paragraph E of Example 18) affords the title compound.

B. 23-O-(tert-Butyldimethylsilyl)-3'',4''-carbonyl-2',3-diacetyl-20-deoxo-20-[(4,4-dioxothiomorpholinyl)imino]-23-demycinosyltylosin.

23-O-(tert-Butyldimethylsilyl)-3'',4''-carbonyl-20-deoxo-20-[(4,4-dioxomorpholino)imino]-23-demycinosyltylosin (1 g.), acetic anhydride (1 ml.), triethylamine (1 ml) and 4-dimethylamino pyridine (1.22 g.) in dry methylene chloride (20 ml.) are allowed to remain at 25° C. for 20 hours. Solvents are removed and the residue is purified on 100 g. silica gel. Elution with 1% methanol in CHCl$_3$ gives the title compound.

C. 3'',4''-Carbonyl-2',3-diacetyl-20-deoxo-20-[(4,4-dioxothiomorpholinyl)imino]-23-demysinosyltylosin.

Following the procedure of paragraph D of Example 1, 23-O-(tert-butyldimethylsilyl)-3'',4''-carbonyl-2',3-diacetyl-20-deoxo-20-[(4,4-dioxothiomorpholinyl)imino]-23-demycinosyltylosin is converted to the desired compound, 3'',4''-carbonyl-2'3-diacetyl-20-deoxo-20-[(4,4-dioxothiomorpholinyl)imino]-23-demycinosyltylosin.

EXAMPLE 21

A. 2'-Acetyl-3'',4''-O-carbonyl-23-demycinosyl-14-dehydroxymethyl-14-formyl-20-deoxo-20-[(4,4-dioxothiomorpholinyl)imino]tylosin.

A solution of 2'-acetyl-3'',4''-O-carbonyl-23-demycinosyl-20-deoxo-20-[(4,4-dioxothiomorpholinyl)imino]tylosin (prepared as in paragraph F of Example 18) (490 mg.) in 2 ml. of dry DMSO (dimethylsulfoxide) and 4 ml. of dry benzene is treated at room temperature with anhydrous pyridine (0.04 ml.), freshly distilled trifluoroacetic acid (0.02 ml.) and dicyclohexylcarbodiimide (310 mg). The mixture is stirred under N$_2$ for 4 hours and the solids were removed by filtration, washed well with more benzene. The organic filtrate is washed three times with distilled water (3×5 ml.), once with saturated brine and dried (MgSO$_4$). Removal of solvent gives the reaction mixture. Purification on 50 g. silica gel column eluted with 10% methanol in CHCl$_3$ gave 2'-acetyl-3'',4''-carbonyl-23-demycinosyl-14-dehydroxymethyl-14-formyl-20-deoxo-20-[(4,4-dioxothiomorpholinyl)imino]tylosin.

B. 2'-Acetyl-3'',4''-O-carbonyl-23-demycinosyl-14-dehydroxymethyl-14-formyl-14,20-dideoxo-14,20-[(4,4-dioxothiomorpholinyl)imino]tylosin.

A mixture of 2'-acetyl-3'', 4''-carbonyl-23-demycinosyl-14-dehydroxymethyl-14-formyl-20-deoxo-20-[(4,4-dioxothiomorpholinyl)imino]tylosin (100 mg.) and 1-N-amino-4,4-dioxothiomorpholine (16 mg.) in dry methylene chloride is stirred at room temperature for 5 hours. Evaporation of solvent gives 2'-acetyl-3'',4''-O-carbonyl-23-demycinosyl-14-dehydroxymethyl-14-formyl-14,20-dideoxo-14,20-[(4,4-thiomorpholinyl)imino]tylosin.

C. 3'',4''-O-Carbonyl-23-demycinosyl-14-dehydroxymethyl-14-formyl-14,20-dideoxo-14,20-[(4,4-dioxothiomorpholinyl)imino]tylosin.

A solution of 2'-acetyl-3'',4''-O-carbonyl-23-demycinosyl-14-dehydroxymethyl-14-formyl-14,20-dideoxo-14,20-[(4,4-dioxothiomorpholinyl)imino]tylosin (80 mg.) in methanol is stored at room temperature for 24 hours. Evaporation of the solvent to dryness gave the titled 3'',4''-O-carbonyl-23-demycinosyl-14-dehydroxymethyl-14-formyl-14,20-dideoxo14,20-[(4,4-dioxothiomorpholinyl)imino]tylosin.

EXAMPLE 22

Repetition of the procedures detailed in the foregoing Examples and the text of the specification and utilizing the appropriate reactants affords the following compounds of this invention:

23-O-demycinosyl-20-[(piperidyl)imino]-20-deoxo-4''-O-acetyltylosin,

23-O-demycinosyl-20-[(4-methylpiperidyl)imino]-20-deoxo-4''-O-acetyltylosin,

23-O-demycinosyl-20-[(4,4-ethylenedioxypiperidyl)imino]-20-deoxo-4''-O-acetyltylosin, 23-O-demycinosyl-20-[(4-benzyloxypiperidyl)imino]-20-deoxo-4''-O-acetyltylosin, 23-O-demycinosyl-20-[(4-methoxypiperidyl)imino]-20-deoxo-4''-O-acetyltylosin, 23-O-demycinosyl-20-[(4-acetyloxypiperidyl)imino]-20-deoxo-4''-O-acetyltylosin, 23-O-demycinosyl-20-[(4-methyl-4-hydroxypiperidyl)imino]-20-deoxo-4''-O-acetyltylosin, 23-O-demycinosyl-20-[(4-ethyl-4-propionyloxypiperidyl)imino]-20-deoxo-4''-O-acetyltylosin, 23-O-demycinosyl-20-[(4-propyl-4-ethoxypiperidyl)imino]-20-deoxo-4″-O-acetyltylosin,
23-O-demycinosyl-20-[(4-phenethylpiperidyl)imino]-20-deoxo-4″-O-acetyltylosin,
23-O-demycinosyl-20-[(4-benzoyloxypiperidyl)imino]-20-deoxo-4″-O-acetyltylosin,
23-O-demycinosyl-20-[(4-butoxycarbonylpiperidyl)imino]-20-deoxo-4″-O-acetyltylosin,
23-O-demycinosyl-20-[(4-carboxypiperidyl)imino]-20-deoxo-4″-O-acetyltylosin,
23-O-demycinosyl-20-[(4-dimethylaminocarbonylpiperidyl)imino]-20-deoxo-4″-O-acetyltylosin,
23-O-demycinosyl-20-[(4-methylpiperazinyl)imino]-20-deoxo-4″-O-acetyltylosin,
23-O-demycinosyl-20-[(4-benzylpiperazinyl)imino-20-deoxo-4″-O-acetyltylosin,
23-O-demycinosyl-20-[(4-phenethylpiperazinyl)imino-20-deoxo-4″-O-acetyltylosin,
23-O-demycinosyl-20-[(morpholino)imino]-20-deoxo-4″-O-acetyltylosin,
23-O-demycinosyl-20-[(thiomorpholino)imino]-20-deoxo-4″-O-acetyltylosin,
23-O-demycinosyl-20-[(4-β-hydroxyethylpiperazinyl)imino]-20-deoxo-4″-O-acetyltylosin,
23-O-demycinosyl-20-[(4-carbamoylpiperidyl)imino]-20-deoxo-4″-O-acetyltylosin,
23-O-demycinosyl-20-[(pyrrolidyl)imino]-20-deoxo-4″-O-acetyltylosin,
23-O-demycinosyl-20-[(homopiperidyl)imino]-20-deoxo-4″-O-acetyltylosin,
23-O-demycinosyl-20-[(2,6-dimethylpiperidyl)imino]-20-deoxo-4″-O-acetyltylosin,
23-O-demycinosyl-20-[(4-oxo-2-thioxo-3-thiazolidinyl)imino]-20-deoxo-4″-O-acetyltylosin,
23-O-demycinosyl-20-[(2,4-dioxoimidazolidinyl)imino]-20-deoxo-4″-O-acetyltylosin,
23-O-demycinosyl-20-[(4-phenylpiperidyl)imino]-20-deoxo-4″-O-acetyltylosin,
23-O-demycinosyl-20-[(4-hydroxy-4-phenylpiperidyl)imino]-20-deoxo-4″-O-acetyltylosin,
23-O-demycinosyl-20-[(4-cyano-4-phenylpiperidinyl)imino]-20-deoxo-4″-O-acetyltylosin,
23-O-demycinosyl-20[4-(p-chlorophenyl)-4-hydroxypiperidyl]-imino-20-deoxo-4″-O-acetyltylosin,
23-O-demycinosyl-20-{[4-(p-chlorophenyl)-3,4-dehydropiperidyl]imino}-20-deoxo-4″-O-acetyltylosin,
23-O-demycinosyl-20-{[4-(o-tolyl)piperazinyl]imino}20-deoxo-4″-O-acetyltylosin,
23-O-demycinosyl-20-{[4-(m-tolyl)piperazinyl]imino-}20-deoxO-4″-O-acetyltylosin,
23-O-demycinosyl-20-[4-(α,α,αtrifluoro-m-toly)-piperazinyl]-imino-20-deoxO-4″-O-acetyltylosin,
23-O-demycinosyl-20-[4-(benzyl)piperazinyl]imino-20-deoxO-4″-O-acetyltosin,
23-O-demycinosyl-20-[4-(p-chlorobenzhydryl)-piperazinyl]imino-20-deoxo-4″-O-acetyltylosin,
23-O-demycinosyl-20-[4-(phenyl)-3,4-dehydropiperidyl]imino-20-deoxo-4″-O-acetyltylosin,
23-O-demycinosyl-20-[(4-benzylpiperidyl)imino]-20-deoxo-4″-O-acetyltylosin,
23-O-demycinoxyl-20-[(4-phenylpiperazinyl)imino]-20-[4-(p-fluorophenyl)piperazinyl]imino-20-deoxo-4″-O-acetyltylosin,
23-O-demycinosyl-20-[4-(O-chlorophenyl)-piperazinyl]imino-20-deoxo-4″-O-acetyltylosin,
23-O-demycinosyl-20-[4-(m-chlorophenyl)-piperazinyl]imino-20-deoxo-4″-O-acetyltylosin,
23-O-demycinosyl-20-{[4-(p-chlorophenyl)-piperazinyl]imino-20-deoxo-4″-O-acetyltylosin,
23-O-demycinosyl-20-{[4-(o-methoxyphenyl)-piperazinyl]imino}-20-deoxo-4″-O-acetyltylosin,
23-O-demycinosyl-20-[4-(p-methoxyphenyl)-piperazinyl]imino-20-deoxo-4″-O-acetyltylosin,
23-O-demycinosyl-20-[4-(p-acetylphenyl)piperazinyl]imino-20-deoxo-4″-O-acetyltylosin,
23-demycinosyl-20-deoxo-20-[(4,4-dioxothiomorpholinyl)imino]-4″-O-propionyltylosin;
23-demycinosyl-20-deoxo-20-[(4,4-dioxothiomorpholinyl)imino]-4″-O-tylosin;
23-demycinosyl-20-deoxo-20-[(4,4-dioxothiomorpholinyl)imino]-4″-O-butyryltylosin;
23-demycinosyl-20-deoxo-20-[(4,4-dioxothiomerpholinyl)imino]-4″-O-iso-butyryltylosin;
23-demycinosyl-20-deoxo-20-[(4,4-dioxothiomorpholinyl)imino]-4″-O-tert-butyltylosin;
23-demycinosyl-20-deoxo-20-[(4,4-dioxothiomorpholinyl)imino]-4″-O-valeryltylosin;
23-demycinosyl-20-deoxo-20-[(4,4-dioxothiomorpholinyl)imino]-3″-O-acetyl-4″-O-iso-valeryltylosin;
23-demycinosyl-20-deoxo-20-[(4,4-dioxothiomorpholinyl)imino]-3″-O-acetyl-4″-O-valeryltylosin;
23-demycinosyl-20-deoxo-20-[(4,4-dioxothiomorpholinyl)imino]-3″-O-acetyl-4″-O-butyryltylosin;
23-demycinosyl-20-deoxo-20-[(4,4-dioxothiomorpholinyl)imino]-3″-O-acetyl-4″-O-propionyltylosin;
2′-O-acetyl-23-demycinosyl-20-deoxo-20-[(4,4-dioxothiomorpholinyl)imino]-4″-O-iso-valeryltylsoin;
4″-O-n-butyryl-23-demycinosyl-20-deoxo-20-[(4,4-dioxothiomorpholinyl)imino]-4″-O-propionyltylosin;
2′-O-acetyl-4″-O-n-butyryl-23-demycinosyl-20-deoxo-20-[(4,4-dioxothiomorpholinyl)imino]-3″-O-propionyltylosin; and
2′,3″-di-O-acetyl-23-demycinosyl-20-deoxo-20-[(4,4-dioxothiomorpholinyl)imino]-4″-iso-valeryltylosin.

The following examples illustrate pharmaceutical formulations incorporating the compounds of this invention. In them, the 23-demycinosyl-20-deoxo-20-[(4,4-dioxothiomorpholinyl)-imino]-4″-O-iso-valeryltylosin may be replaced by an equivalent amount of any of the other compounds of this invention.

EXAMPLE 23

| Capsule | |
|---|---|
| 23-demycinosyl-20-deoxo-20-[(4,4-dioxothiomorpholinyl)imono]-4″-O—iso-valeryltylosin | 250.00 mg. |
| Lactose | 248.75 mg. |
| Magnesium Stearate | 1.25 mg. |
| | 500.00 mg. |

Blend the active ingredient and the lactose. Add the magnesium stearate and mix. Fill capsule.

EXAMPLE 24

| Oral Suspension (to give a dose of 125 mg/5 ml) | |
|---|---|
| 23-demycinosyl-20-deoxo-20-[(4,4-dioxothiomorpholinyl)imino]-4″-O—iso-valeryltylosin | 25.00 gms |
| Magnesium Aluminum Siliate | 9.50 gms |

45

-continued

| Oral Suspension (to give a dose of 125 mg/5 ml) | |
|---|---|
| Sodium Carboxymethylcellulose U.S.P | 2.50 gms |
| Flavor | q.s. |
| Color | q.s. |
| Methylparaben, U.S.P. | 0.90 gms |
| Propylparaben, U.S.P. | 0.20 gms |
| Polysorbate 80, U.S.P. | 1.00 gms |
| Sorbitol Solution, U.S.P. | 500.00 gms |
| Water, q.s. | 1000.00 ml |

1. Heat 200 ml of water to boiling, and dissolve in it one-half of the parabens. Cool to about 70° C., then mix in the Polysorbate 80. Sprinkle in the silicate, stirring until a uniform smooth suspension results.

2. Heat an additional 200 ml. of water to boiling and dissolve in it the remainder of the parabens. Dispense the CMC in this until a smooth gel results. Mix in the Sorbitol Solution. Then dissolve the sodium citrate.

3. Add the product of Step 2 to that of Step 1 slowly with constant stirring. Cool the mixture to 25° C. Add the active ingredient, flavor, and color, mixing thoroughly. Add sufficient quantity of water to make the total volume 1000 ml.

EXAMPLE 25

| Topical Ointment | |
|---|---|
| 23-demycinosyl-20-deoxo-20-[(4,4-dioxothiomorpholinyl)imino]-4''-O—iso-valeryltylosin | 10 gms |
| Petrolatum | 990 gms |
| | 1000 gms |

Melt the petroleum. Slurry the antibiotic with about 10% of the petrolatum and pass through a colloid mill. Mix the milled slurry with the remainder of the molten petrolatum. Allow to cool.

EXAMPLE 26

| Topical Cream | |
|---|---|
| 23-demycinosyl-20-deoxo-20-[(4,4-dioxothiomorpholinyl)imino]-4''-O—iso-valeryltylosin | 10 gms |
| Stearic Acid | 200 gms |
| Sorbitan Monostearate | 104 gms |
| Sorbitan Monoleate | 20 gms |
| Polyoxyethylene Sorbitan Monolaurate | 56 gms |
| Water, q.s. | 100 ml |

EXAMPLE 26

| Topical Cream | |
|---|---|
| 23-demycinosyl-20-deoxo-20-[(4,4-dioxothiomorpholinyl)imino]-4''-O—iso-valeryltylosin | 10 gms |
| Stearic Acid | 200 gms |
| Sorbitan Monostearate | 104 gms |
| Sorbitan Monoleate | 20 gms |
| Polyoxyethylene Sorbitan Monolaurate | 56 gms |
| Water, q.s. | 100 ml |

1. Heat the stearic acid, sorbitan monostearate, sorbitan monoleate, and polyoxyethylene sorbitan monolaurate to 65° C.

2. Heat about 90% of the water to 70° C.

46

3. Add the water of Step 2 to the mixture of Step 1 and mix to form a cream base.

4. Slurry the active ingredient with about 10% of the water and pass through a colloid mill.

5. Add the milled slurry to the molten base and mix. Allow to cool.

What is claimed is:

1. A compound of the formula

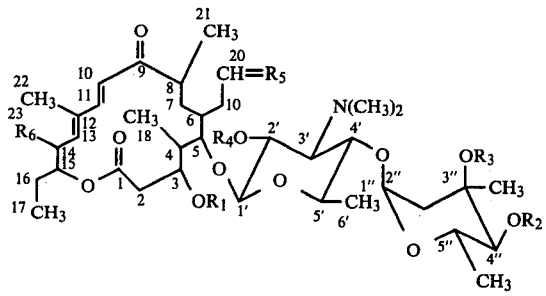

wherein $R_1$ is hydrogen or an acyl group selected from alkanoyl of 2 to 5 carbon atoms, palmityl, stearyl, lauryl, oleyl, chloroacetyl, benzoyl, adamantanecarbonyl, cyclopropanecarbonyl, cyclohexanecarbonyl, β-cyclohexylpropionyl, phenylacetyl, phenoxyacetyl, mandelyl, 2-thienylacetyl, alkyl-, aryl- and aralkylsulfonyl, substituted aryl- and aralkylsulfonyl, wherein the substituents on the aryl portions are halogen, nitro and alkoxy groups, succinyl, maleyl, fumaryl, malonyl and phthalyl;

$R_2$ is acyl, wherein acyl is as defined in $R_1$;

$R_3$ is hydrogen or acyl, wherein acyl is as defined in $R_1$; or $R_2$ and $R_3$ are together a carbonyl group linking the 3''- and 4''-hydroxyl groups;

$R_4$ is hydrogen or acyl, wherein acyl is as defined in $R_1$;

$R_5$ is selected from the group consisting of N-NH-aralkyl,

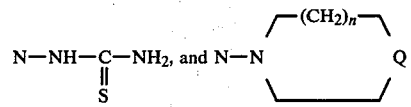

wherein n is 0-2, and

Q is selected from the group consisting of $CH_2$, $CHR_7$, $CHR_8$, $CR_7R_8$, $NR_6$, O, S, $SO_2$, CHOH, $CHOR_7$,

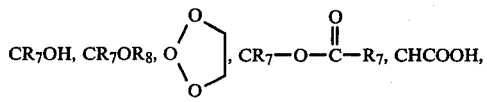

wherein $R_7$ and $R_8$ are independently selected from the group consisting of ($C_1$-$C_6$) alkyl, ($C_7$-$C_{10}$) aralkyl and ($C_6$-$C_{10}$) aryl including X-substituted aryl and aralkyl, wherein X is halogen, trifluoromethyl, ($C_1$-$C_6$) alkoxy, or ($C_1$-$C_6$) alkylcarbonyl; $R_6$ is methyl, hydroxymethyl, fluoromethyl, chloromethyl, bromomethyl, iodomethyl, di ($C_1$-$C_6$)

alkylamino, acyloxymethyl, CHO or a group of the formula CH=R$_5$ wherein R$_5$ is as hereinbefore defined; and the pharmaceutically acceptable salts thereof.

2. A compound according to claim 1 wherein R$_5$ is a group of the formula

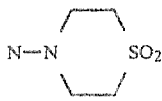

3. A compound according to claim 1 or 2 wherein R$_6$ is a methyl or hydroxymethyl group.

4. A compound according to claim 1 or 2 wherein R$_1$, R$_3$ and R$_4$ are hydrogen and R$_2$ is an acyl group selected from the group consisting of acetyl, propionyl, n-butyryl and iso-valeryl.

5. A compound according to claim 1 or 2 wherein R$_1$ is acetyl, R$_3$ and R$_4$ are hydrogen and R$_2$ is an acyl group selected from the group consisting of acetyl, propionyl, n-butyryl and iso-valeryl.

6. A compound according to claim 1 or 2 wherein R$_1$ and R$_3$ are hydrogen and R$_2$ and R$_4$ are acyl groups selected from the group consisting of acetyl, propionyl, n-butyryl and iso-valeryl.

7. A compound according to claim 1 or 2 wherein R$_1$ and R$_4$ are hydrogen, and R$_2$ and R$_3$ are acyl groups selected from the group consisting of acetyl, propionyl, n-butyryl and iso-valeryl.

8. A compound according to claim 1 or 2 wherein R$_1$ is hydrogen and R$_2$, R$_3$ an R$_4$ are acyl groups selected from the group consisting of acetyl, propionyl, n-butyryl and iso-valeryl.

9. A compound according to claim 1 or 2 wherein R$_2$ and R$_3$ are a bridging carbonyl group.

10. A compound according to claim 2 which is 23-demycinosyl-20-deoxo-20-[(4,4-dioxothiomorpholinyl)imino]-4''-O-iso-valeryltylosin.

11. A compound according to claim 2 which is 4''-O-acetyl-23-demycinosyl-20-deoxo-20-[(4,4-dioxo-thiomorpholinyl)imino]tylosin.

12. A compound according to claim 2 which is 2',4''-di-O-acetyl-23-demycinosyl-20-deoxo-20-[(4,4-dioxothiomorpholinyl)imino]tylosin.

13. A compound according to claim 2 which is 2'-O-acetyl-23-demycinosyl-20-deoxo-20-[(4,4-dioxothiomorpholinyl)imino]-4''-O-iso-valeryltylosin.

14. A compound according to claim 2 which is 4''-O-n-butyryl-23-demycinosyl-20-deoxo-20-[(4,4-dioxomorpholinyl)imino]-3''-O-propionyltylosin.

15. A compound according to claim 2 which is 2'-O-acetyl-4''-O-n-butyryl-23-demycinosyl-20-deoxo-20-[(4,4-dioxothiomorpholinyl)imino]-3''-O-propionyltylosin.

16. A compound according to claim 2 which is 3''-O-acetyl-23-demycinosyl-20-deoxo-20-[(4,4-dioxothiomorpholinyl)imino]-4''-O-iso-valeryltylosin.

17. A compound according to claim 2 which is 2',3''-di-O-acetyl-23-demycinosyl-20-deoxo-20-[(4,4-dioxothiomorphinyl)imino]-4'-O-iso-valeryltylosin.

18. A compound according to claim 2 which is 3'',4''-O-carbonyl-2',3-diacetyl-20-deoxo-20-[(4,4-dioxothiomorpholinyl)imino]-tylosin.

19. A compound according to claim 2 which is 2'-O-acetyl-3'',4''-O-carbonyl-23-demycinosyl-20-deoxo-20-[(4,4-dioxothiomorpholinyl)imino]-tylosin.

20. A method of eliciting an antibacterial response in a mammal having a gram positive bacterial infection which comprises administering to the mammal a therapeutically effective quantity of a compound according to claim 1.

21. A method according to claim 20 wherein R$_5$ is a group of the formula

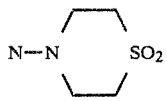

22. A method according to claim 20 or 21 wherein R$_6$ is a methyl or hydroxymethyl group.

23. A method according to claim 20 wherein the compound utilized is 23-demycinosyl-20-deoxo-20-[(4,4-dioxothiomorpholinyl)imino]-4''-O-isovaleryl-tylosin.

24. A method according to claim 20 wherein the compound utilized is 2',4''-O-acetyl-23-demycinosyl-20-deoxo-20-[(4,4-dioxothiomorpholinyl)imino]-tylosin.

25. A method according to claim 20 wherein the compound utilized is 2',4''-di-O-acetyl-23-demycinosyl-20-deoxo-20-[(4,4-dioxothiomorpholinyl)imino]-tylosin.

26. A method according to claim 20 wherein the compound utilized is 2'-O-acetyl-23-demycinosyl-20-deoxo-20-[(4,4-dioxothiomorpholinyl)imino]-4''-O-isovaleryltylosin.

27. A method according to claim 20 wherein the compound utilized is 4''-O-n-butyryl-23-demycinosyl-20-deoxo-20-[(4,4-dioxothiomorpholinyl)imino]-3''-O-propionyltylosin.

28. A method according to claim 20 wherein the compound utilized is 2'-O-acetyl-4''-O-n-butyryl-23-demycinosyl-20-[(4;4-dioxothiomorpholinyl)imino]-3''-O-propionyltylosin.

29. A method according to claim 20 wherein the compound utilized is 3''-O-acetyl-23-demycinosyl-20-deoxo-20-[(4,4-dioxothiomorpholinyl)imino]-4''-O-isovaleryltylosin.

30. A method according to claim 20 wherein the compound utilized is 2',3''-di-O-acetyl-23-demycinosyl-20-deoxo-20-[(4,4-dioxothiomorpholinyl)imino]-4''-O-iso-valeryltylosin.

31. A method according to claim 20 wherein the compound utilized is 3'',4''-O-carbonyl-2'3-diacetyl-20-deoxo-20-[(4,4-dioxothiomorpholinyl)imino]-23-demyinosyltylosin.

32. A method according to claim 20 wherein the compound utilized is 2'-O-acetyl-3'',4''-O-carbonyl-23-demycinosyl-20-[(4,4-dioxothiomorpholinyl)imino]tylsoin.

33. A pharmaceutical composition adapted for the treatment of a mammal having a gram positive bacterial infection which comprises a therapeutically effective quantity of a compound according to claim 1 or 2 in admixture with a pharmaceutically acceptable carrier therefor.

34. A pharmaceutical composition according to claim 33 which comprises 23-demycinosyl-20-deoxy-20-[(4,4-dioxothiomorpholinyl)imino]-4''-O-iso-valeryltylosin.

35. A pharmaceutical composition according to claim 33 which comprises 4''-O-acetyl-23-demycinosyl-20-deoxo-20-[(4,4-dioxothiomorpholinyl)imino]-tylosin.

36. A pharmaceutical composition according to claim 33 which comprises 2'4"-di-O-acetyl-23-demycinosyl-20-deoxo-20-[(4,4-dioxothiomorpholinyl)imino]-tylosin.

37. A pharmaceutical composition according to claim 33 which comprises 2'-O-acetyl-23-demycinosyl-20-deoxo-20-[(4,4-dioxothiomorpholinyl)imino]-4"-O-isovaleryltylosin.

38. A pharmaceutical composition according to claim 33 which comprises 4"-O-n-buryryl-23-demycinosyl-20-deoxo-20-[(4,4-dioxothiomorpholinyl)imino]-3"-O-propionyltylosin.

39. A pharmaceutical composition according to claim 33 which comprises 2'-O-acetyl-4"-O-n-butyryl-23-demycinosyl-20-deoxo-20-[(4,4-dioxothiomorpholinyl)imino]-3"-O-propionyltylosin.

40. A pharmaceutical composition according to claim 33 which comprises 3"-O-acetyl-23-demycinosyl-20-deoxo-20-[(4,4-dioxothiomorpholinyl)imino]-4"-O-isovaleryltylosin.

41. A pharmaceutical composition according to claim 33 which comprises 2',3"-di-O-acetyl-23-demycinosyl[(4,4-dioxothiomorpholinyl)imino]-4"-O-isovaleryltylosin.

42. A pharmaceutical composition according to claim 33 which comprises 3",4"-O-carbonyl-2',3-diacetyl-20-deoxo-20-[(4,4-dioxothiomorpholinyl)imino]-23-demycinosyl-tylosin.

43. A pharmaceutical composition according to claim 33 which comprises 2'-O-acetyl-3",4"-O-carbonyl-23-demycinosyl-20-deoxo-20-[(4,4-dioxothiomorpholinyl)imino]-tylosin.

44. A pharmaceutical composition according to claim 33 adapted for oral administration.

45. A pharmaceutical composition according to claim 33 adapted for topical administration.

46. A pharmaceutical composition according to claim 33 adapted for injectable administration.

47. A compound of the formula

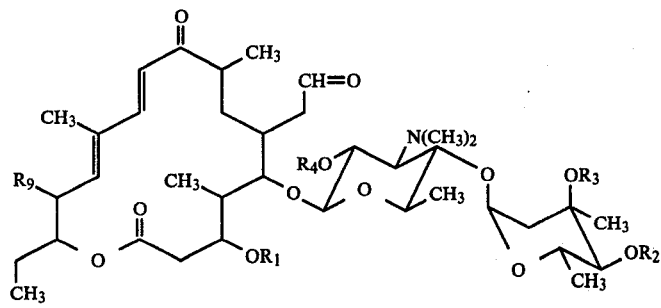

wherein $R_9$ is fluoromethyl, chloromethyl, bromomethyl, iodomethyl, acyloxymethyl, CHO or di ($C_1$–$C_6$) alkylamino;

$R_1$ is hydrogen or acyl, wherein acyl is as defined in claim 1;

$R_2$ is acyl, wherein acyl is as defined in claim 1;

$R_3$ is hydrogen or acyl, wherein acyl is as defined in claim 1;

$R_4$ is hydrogen or acyl, wherein acyl is as defined in claim 1; and the pharmaceutically acceptable salts thereof.

* * * * *